US010555374B2

(12) United States Patent
Schryver et al.

(10) Patent No.: US 10,555,374 B2
(45) Date of Patent: Feb. 4, 2020

(54) SYSTEMS, DEVICES, AND METHODS FOR AUTOMATED SAMPLE THAWING

(71) Applicant: BioLife Solutions, Inc., Bothell, WA (US)

(72) Inventors: Brian Schryver, Redwood City, CA (US); David Shannon, Sammamish, WA (US)

(73) Assignee: BioLife Solutions, Inc., Bothell, WA (US)

(*) Notice: Subject to any disclaimer, the term of this patent is extended or adjusted under 35 U.S.C. 154(b) by 451 days.

(21) Appl. No.: 14/712,120

(22) Filed: May 14, 2015

(65) Prior Publication Data
US 2015/0334774 A1   Nov. 19, 2015

Related U.S. Application Data

(60) Provisional application No. 61/994,586, filed on May 16, 2014, provisional application No. 62/042,669, filed on Aug. 27, 2014.

(51) Int. Cl.
*H05B 1/02* (2006.01)
*A47J 36/24* (2006.01)
(Continued)

(52) U.S. Cl.
CPC ............. *H05B 1/025* (2013.01); *A47J 36/24* (2013.01); *A47J 36/2483* (2013.01); *A47J 36/32* (2013.01);
(Continued)

(58) Field of Classification Search
CPC ....... H05B 1/025; A47J 36/24; A47J 36/2483; A47J 36/32; B01L 7/00; G01K 3/10; G01K 7/22
(Continued)

(56) References Cited

U.S. PATENT DOCUMENTS 1,623,209 A    4/1927 Frank
5,999,701 A    12/1999 Schmidt
(Continued)

FOREIGN PATENT DOCUMENTS

EP          3227659      10/2017
JP     2011-513314 A    4/2011
(Continued)

OTHER PUBLICATIONS

PCT/US2015/030852, "International Preliminary Report on Patentability", dated Dec. 1, 2016, 8 pages.
(Continued)

*Primary Examiner* — Dana Ross
*Assistant Examiner* — Joseph M Baillargeon
(74) *Attorney, Agent, or Firm* — Kilpatrick Townsend & Stockton LLP

(57) ABSTRACT

The present invention generally relates to thawing a cryogenically frozen sample. The systems, devices, and methods may be used to heat a sample holder, the sample holder configured to receive a sample container holding the frozen sample. A sample thaw start time may be identified by measuring a temperature of the sample container and/or a temperature of the sample. A sample thaw end time may be calculated as a function of the sample thaw start time. In some embodiments, the same thaw start time may be identified by a significant change in a first derivative of a warming curve of recorded temperature measurements. The sample end time may be calculated by adding a constant to the sample thaw start time. The constant may be the average sample thaw time per the sample container.

25 Claims, 27 Drawing Sheets

(51) Int. Cl.
*A47J 36/32* (2006.01)
*B01L 7/00* (2006.01)
*G01K 3/10* (2006.01)
*G01K 7/22* (2006.01)

(52) U.S. Cl.
CPC .............. *B01L 7/00* (2013.01); *G01K 3/10* (2013.01); *G01K 7/22* (2013.01)

(58) Field of Classification Search
USPC ............ 219/439, 535, 536, 385, 459.1, 429; 422/562; 435/305.1, 305.3; 436/180; 165/80.2, 185; 206/569, 370, 443, 807; 211/74; 220/507, 446, 592.2; 229/927; 62/457.1, 440; 222/93; 248/311.2, 248/316.3, 313; 392/470
See application file for complete search history.

(56) References Cited

U.S. PATENT DOCUMENTS

| | | | | |
|---|---|---|---|---|
| 6,082,114 | A * | 7/2000 | Leonoff | A47J 31/005 62/3.64 |
| 8,136,985 | B2 * | 3/2012 | Lane | A61B 5/01 374/121 |
| 8,563,907 | B2 * | 10/2013 | Bushman | G21F 5/015 219/459.1 |
| 2004/0065658 | A1 | 4/2004 | Damiano et al. | |
| 2007/0125677 | A1 * | 6/2007 | Oronsky | B01L 3/5082 206/446 |
| 2008/0047948 | A1 * | 2/2008 | Rosenbloom | A47J 36/2483 219/386 |
| 2011/0011850 | A1 | 1/2011 | Rosenbloom et al. | |
| 2011/0309086 | A1 | 12/2011 | Arnitz et al. | |
| 2012/0095441 | A1 | 4/2012 | Pendlebury | |
| 2013/0084227 | A1 | 4/2013 | Cole et al. | |
| 2015/0125138 | A1 * | 5/2015 | Karnieli | A01N 1/0242 392/441 |

FOREIGN PATENT DOCUMENTS

| | | |
|---|---|---|
| WO | 9909137 | 2/1999 |
| WO | 2013-014411 A | 1/2013 |
| WO | 2013014411 | 1/2013 |
| WO | 2013126379 | 8/2013 |
| WO | 2014068508 | 5/2014 |
| WO | 2016087873 | 6/2016 |

OTHER PUBLICATIONS

PCT/US2015/030852, "International Search Report and Written Opinion", dated Oct. 2, 2015, 12 pages.
PCT/US2015/030852, "Invitation to Pay Add'l Fees and Partial Search Report", dated Jul. 30, 2015, 2 pages.
U.S. Appl. No. 14/712,120, "Final Office Action", dated Jan. 26, 2018, 22 pages.
U.S. Appl. No. 14/712,120, "Non-Final Office Action", dated Jul. 27, 2017, 18 pages.
U.S. Appl. No. 14/712,120, "Non-Final Office Action", dated Jul. 17, 2018, 24 pages.
EP15793552.9, "Extended European Search Report", dated Feb. 5, 2018, 9 pages.
Triana et al., "Thawing of Cryopreserved Hematopoietic Progenitor Cells from Apheresis With a New Dry-Warming Device", Transfusion, vol. 53, No. 1, Jan. 2013, pp. 85-90.

* cited by examiner

Top View

SECTION A-A
SCALE 1 : 2

Front Cross-section

TOP VIEW

SECTION A-A

FRONT CROSS-SECTION

SYSTEMS, DEVICES, AND METHODS FOR AUTOMATED SAMPLE THAWING

CROSS-REFERENCE TO RELATED APPLICATIONS

The present application claims priority to U.S. Provisional Application No. 61/994,586 filed May 16, 2014 and U.S. Provisional Application No. 62/042,669 filed Aug. 27, 2014, the full disclosures which are incorporated herein by reference in their entirety for all purposes.

BACKGROUND OF THE INVENTION

The present invention generally relates to the cryogenic preservation of cells and more specifically to systems, devices, and methods for the recovery of cryogenically-preserved cells and tissue.

Cryogenic preservation of cells in suspension is a well-established and accepted technique for long term archival storage and recovery of live cells. As a general method, cells are suspended in a cryopreservation media typically including salt solutions, buffers, nutrients, growth factors, proteins, and cryopreservatives. The cells are then distributed to archival storage containers of the desired size and volume, and the containers are then reduced in temperature until the container contents are frozen. Typical long-term archival conditions include liquid nitrogen vapor storage where temperatures are typically between −196 and −150 degrees Celsius.

The successful recovery of live cells preserved by such methods may be dependent upon minimizing injurious ice crystal growth in the intracellular region during both the freezing and thawing processes. Some advances have been made to reduce intracellular ice crystal growth during the freezing process. For example, intracellular ice crystal growth may be reduced by adding a cryoprotectant compound to the tissues or cell suspension solution that inhibits ice crystal nucleation and growth both extracellularly and intracellularly. Additionally, the growth of intracellular ice can be controlled through management of the rate of sample temperature reduction. During the freezing process extracellular ice crystal formation will exclude solutes and cells from the developing ice crystal structure thereby concentrating the solutes and cells in the remaining liquid phase. The increase in solute concentration will establish an osmotic potential that will promote the dehydration of the cells while allowing time for cell membrane-permeable cryoprotectants to equilibrate in concentration within the intracellular volume. As the freezing process progresses a temperature will be reached at which the high solute concentration will solidify in a glass state with minimal size of ice crystal nuclei within the intracellular volume. The solid-state cell suspension is then further reduced in temperature until the cryogenic storage temperature is reached. At this temperature molecular activity is sufficiently reduced that the cells may be stored indefinitely. For optimal cell recovery following cryogenic storage, the rate of temperature reduction during the freezing process must fall within a range of values. If the temperature reduction rate is too fast, the cells may freeze before the level of intracellular water has been sufficiently reduced, thereby promoting the growth of intracellular ice crystals. If the rate of temperature reduction is too slow, the cells may become excessively dehydrated and the extracellular solute concentration may become too high, with both cases leading to damage of critical cellular structures. For this reason, the temperature reduction rate during the freezing process is typically controlled. For example, one method of controlling the rate of temperature reduction includes surrounding the sample with an insulating material and placing the assembly in a static temperature environment, while another method includes placing the exposed sample container into an isolation chamber in which the interior temperature is reduced at a controlled rate.

Returning the sample from the cryogenic archival state involves thawing the sample to a fully liquid state. During the thawing process, again the rate of temperature change can influence the viability of the cryogenically preserved cells. The solid contents of the sample storage vessels contains large islands of crystallized water which are interposed by channels of glass state aqueous solutes intermixed with small nuclei of ice crystals. During the transition from the cryogenic storage temperature to the conclusion of the phase change to a completely liquid state, there is an opportunity for rearrangement of the water molecules within the sample including a thermodynamically favored extension of the small ice nuclei within the cells. As the growth of the intracellular ice crystals have an associated potential for cell damage, and as the degree of crystal growth is a time-dependent the phenomenon, minimizing the time interval of the transition through the phase change is desirable. A rapid slew rate in the sample vessel temperature is typically achieved by partial submersion of the vessel in a water bath set to a temperature of approximately 37 degrees Celsius. Although a faster rate of thawing can be achieved by increasing the temperature of the bath, submersion of the vessel in the bath will establish temperature gradients within the vessel with the highest temperatures being located at the vessel wall. As a result, transient thermodynamic states will occur wherein the temperature of the liquid-solid mixture will exceed the melting temperature even though frozen material is present in close proximity. The intra-vessel temperature gradient therefore places an upper limit on the bath temperature. In addition, as common cryoprotectants have a known toxic influence on the cells, differential exposure of the cells in the liquid state with respect to time and temperature allows for variation in the viability of the cells upon completion of the thaw process. As the toxic effect of the cryoprotectants is enhanced at elevated temperatures, a lower liquid temperature is desirable. For this reason, common thawing protocols typically include a rapid thaw phase that is terminated when a small amount of solid material still remains in the sample container. Following removal from the water bath, the sample temperature will quickly equilibrate to a temperature that is near to the phase change temperature. Thawing protocols typically seek to minimize the duration at which the thawed sample is held in a state where the cryoprotectant is concentrated, and subsequent steps to dilute the sample or exchange the cryopreservation media for culture media are commonly applied in as short of an interval as possible. As the current methods and solutions for thawing of cryogenic samples in sample vials is dependent upon the methodology, protocols, and equipment that differs on an individual basis, no current method is available by which the vial thawing process can be standardized across the academic or clinical community. Accordingly, improvements may be desired.

SUMMARY OF THE INVENTION

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

For thawing cells, conventional practice is to warm the cells quickly in a warm water bath (e.g., 37 deg. C.) to just about the point at which the last bit of ice is about to melt and then to dilute the cells slowly into growth media. If the sample is allowed to get too warm, the cells may start to metabolize, and be poisoned by the DMSO (dimethyl sulfoxide) that is used in the freezing process. Generally, the thawing of cryogenically preserved cells and tissue is performed by lab technicians and the applied protocol can not only vary between each lab technician, but may also be technique dependent. The completion of sample thaw is generally subjectively judged by each individual technician and may result in variation in the thaw rate or samples which have been allowed to become too warm. Although a repeatable thawing profile is theoretically possible to achieve using a bath and manual control of the vial insertion, expected variance in both technique and degree of protocol compliance, particularly combined with the requirement to frequently remove the vial from bath to monitor the thaw status, makes deviation from the standard profile a near certainty. The removal of the vial from the bath interrupts the thermal energy transfer from the bath water to the vial and visual assessment of the thaw status is often difficult and may be complicated by the presence of vial labels and printed writing surfaces that are provided as integrated features of the vial product. Further water baths are also a source of contamination and inadvertent submersion of the vial body-cap junction can result in the introduction of bath liquid into the vial contents during removal of the vial cap.

Systems, devices, and methods that provide simplified, automated, and/or more consistent sample thawing may be advantageous and may increase cell recovery. Furthermore, a device that functions autonomously in combination with a methodology that is easily configured and performed may provide a manner by which a standard thawing process may be integrated across academic and/or clinical communities, thereby eliminating a source of variance in experimental results and therapeutic outcome. Devices and methods that will provide automation and standardization of the thawing process for sample vials may resolve multiple obstacles in the execution of this achievement. The embodiments of the present invention may address one or more of these issues. To replicate a thawing process in which the warming phase is terminated after substantial thawing (e.g., while a small portion of the sample is still in the solid phase or when the sample substantially completes the phase change from solid to liquid), a thawing system may use one or more sensors and/or thawing algorithms to predict various stages of the thawing process. In some embodiments, as there is a range of susceptibility to the combined effects of intracellular ice crystal growth during thawing, cryoprotectant exposure, and liquid state temperature elevation during the thaw process, obtaining a consistent recovery state for a given cell type or cell mixture may be dependent upon close control of the thawing temperature increase profile with respect to time.

Accordingly, in some embodiments of the invention, systems and methods may be provided for thawing samples under consistent and uniform conditions. As samples stored under cryogenic temperatures will often be in a location that is remote from the heater in which recovery operations will be conducted, a system must be established to regulate the temperature of the sample during transport to ensure that the sample does not begin thawing prematurely or spend an unnecessarily long interval at temperatures above −75° C. Although ideally the temperature of a sample in the time interval between the retrieval from cryogenic storage and the start of the thawing process should be maintained below the glass transition temperature of the cryogenic storage fluid (approximately −150° C.), however for a number of cell cultures, a temporary storage interval in the temperature range of −150° C. to −75° C. for at least several days may be utilized without a detectable decrease in cell viability upon recovery and culture. For such samples, a transportation and temporary holding temperature of approximately −75° C. is readily applied as the temperature coincides with the phase change temperature of solid carbon dioxide which may be used as a refrigerant. For more temperature-sensitive samples, a transportation and temporary storage temperature of approximately −195° C. may be obtained by using liquid nitrogen as a refrigerant. A system may include a container for a sample vial that will allow thermal equilibration of the sample at a temperature at or below −75° C. The system may also include a container for the sample vessel for holding and thawing a sample. In some embodiments, a contact surface of the sample holder (hereafter referred to as a "warming block") that is in physical contact with the outer surface of the sample vessel may be heated to a constant temperature (e.g., 37° C.). A micro-processor may be coupled with the sample container holder and the processor may use a predictive thawing model to identify an end time of the sample thawing process. The predictive thawing model may identify a thaw completion time based in part on the starting time of the thawing process. In some embodiments, the thaw completion time may be obtained from a pre-determined average thaw time for a particular sample container format containing a particular sample volume payload for a particular warming temperature, as by use of reference to a look-up data table derived from experimental values. In other embodiments the instant invention may receive data from a temperature sensor that rests in contact with the exterior surface of the sample vessel, and may determine the beginning of the sample solid to liquid phase conversion based on the temperature data, and in combination with a phase conversion interval that is experimentally derived for an equivalent sample mass and vial configuration, predict the time at which the phase change conversion will be completed or be near to completion. In other embodiments, the thaw completion time may be determined entirely through a predictive calculation based upon analysis of data received from a temperature sensor that is operably coupled with the sample vessel (e.g., in direct contact with the exterior surface, through use of a non-contact infrared sensor, or the like). In other embodiments, the approach of the end of the phase change interval will be detected by a noise signal in the data stream derived from random motion of the solid phase remnant in the vial as detected by a temperature sensor that is operably coupled with the sample vessel. In some embodiments the vial exterior surface temperature sensor is in contact with the side of the vessel while in other embodiments, the sensor is in contact with the bottom surface of the vessel. In other embodiments, the temperature of the sample vessel contents will be measured by a sensor that is physically centered in the interior of the vessel and is isolated from the contents by a covering of material that is a continuous extension of the vessel exterior. In some embodiments, the external vial surface sensor may be a component of the thawing device, while in other embodiments the sensor may be a component of the vessel. When the sensor is a component of the sample vessel, the sensor may be include a connection (e.g., electrical, radio, or optic connection) to the thawing device by which data may be exchanged. In some embodiments, the data stream may comprise thermometric data exclusively while in other embodiments, the data stream may comprise additional information such as, but not limited to, vessel tracking information, vial contents history and composition, and chain of custody history. In some embodiments the temperature sensors may be thermocouples, thermistors, and resistance sensors, while in other embodiments, the vial temperature may be detected by an infra-red non-contact temperature detector.

Some embodiments may comprise one or more temperature transducers by which the temperature of the warming block may be monitored. In some embodiments the temperature of the warming block is controlled by a microprocessor receiving temperature signal feedback from the warming block temperature transducers. The system may include one or more transducers for recording one or more temperatures of the sample and/or the sample container. In some embodiments one or more transducers may be provided for measuring and/or recording the temperature of the exterior surface of the sample container. In some embodiments, one or more transducers may be provided for measuring and/or recording the temperature of the sample.

In some embodiments, the system may have a user interface and may receive a user input via the user interface before recording temperatures from the sample and/or sample container. Alternatively, the system may be automatically triggered to begin recording temperatures from the sample and/or sample container after the sample container is inserted into the sample holder. In some embodiments, the system may use the automatic triggering mechanism alone to signal the beginning of the thaw interval. In some embodiments, the system may use the automatic triggering mechanism to signal the beginning of the thaw interval, and in combination with the starting signal use a time value constant to determine the completion of the thaw process. In other embodiments, an algorithmic analysis of temperature measurements of the outer surface of the sample container is used to determining the start and end-point of the interval of the sample solid to liquid phase change. The temperature increase during the interval where the sample is exclusively in a solid phase may be modeled by a linear time-invariant lumped system equation wherein a time constant value controls the rate of temperature increase. In other embodiments, the start of the thaw interval may be determined by calculation of the time constant variable for a linear time-invariant lumped system equation such that the temperature output values of the equation will overlay the solid phase portion of the time-temperature data received from the vial surface temperature sensor, and by using a multiple of the time constant value to indicate the time of commencement of the solid to liquid phase change. In other embodiments, the automated thawing system may use a combination of thaw insertion signal, a time value, and an algorithmic analysis of the sample container surface temperature data to determine the beginning and the end-point of the thaw process.

In some embodiments, following retrieval from the cryogenic storage system, the temperature of the frozen sample vial is allowed to equilibrate to a temperature of approximately −78° C. to −75° C. by placing the sample into an aluminum alloy holder (the "equilibration block") that is resting on and surrounded by dry ice. In this embodiment, the vial is removed from the equilibration block and immediately placed into the warm block of known and constant temperature. Using this embodiment and method, a very uniform and predictable thaw interval (the "total thaw interval") can be determined for a given vial geometry and payload, thereby allowing a thawing completion to be predicted exclusively by a time interval following insertion into the warming block. In other embodiments, following temperature equilibration in the equilibration block and insertion into the warming block, the thawing interval may be determined by a combination of total thaw time interval and algorithmic analysis of the vial exterior temperature data, thereby providing an internal self-reference check for the thaw interval prediction system.

In some embodiments, the warming block is configured to accept multiple sample container geometries (e.g., vials, vessels, bags, or the like) by providing multiple receiver wells of the appropriate dimensions. In other embodiments, the warming block is configured to accept only one sample container and is dedicated to a thawing sample container of the appropriate dimensions for that warming block only. In other embodiments the warming block is designed to accept multiple sample container sizes and geometries by the exchange of appropriate vial adapters designed for the specific sample containers. Optionally, the warming block may utilize morphing contacts, flexible wraps, rotating block faces, heat rollers, IR heaters, and/or scroll jaw chucks for accepting multiple sample container sizes and geometries. In some embodiments the system may adjust a completion time based in-part on a sample container type. Optionally, the system may be configured to automatically determine the type of sample container being thawed. For example, some sample containers may include 1D barcodes, 2D barcodes, RFID chips, or other computer readable indicia that are readable by a barcode reader of the system or a RFID chip sensor of the system. The container's barcode, RFID chip, or other computer readable indicia may be linked to a thawing profile of the container and the system may automatically determine a thawing interval specific for the container or otherwise determine a thaw end time specific for the type of container (e.g., through look up tables, formulas, or the like). In some embodiments, a look-up table may be defined by a mathematical function. Optionally, the system may receive user input via a user interface for defining the type of sample container being thawed. In some embodiments, the thaw end time and total thaw time may be determined using the starting vessel external temperature, the temperature of the warming blocks (e.g., non-pliable solid material), and the vessel type.

In some embodiments, the sample vial-receiving well of the warming block comprises a thermally conductive pliable material lining to provide a uniform and repeatable level of thermal contact with the sample container. In some embodiments the warming block is divided into two parts such that when the two parts are separated, the interior walls of the sample container receiving well do not contact or have minimal contact with the sample container, thereby facilitating the insertion and removal of the sample container from the well, and providing a manner with which to initiate the thawing process at a defined moment, in addition to providing a way of interrupting the flow of thermal energy from the warming block to the sample vial. In some embodiments, the sample vial-receiving well of the warming block is divided by a vertical plane that is coincident with the central axis of the sample receiving well. In other embodiments the warming block is divided into more than two parts (e.g., three parts, four parts, or more) that allow a space to be selectively introduced between the warming block sample vial receiver well wall and sample vial exterior by transient lateral or angular displacement of the warming block segments. In some embodiments, the warming block segments are constrained by mechanical linkages such as slide mechanisms, hinged joints, kinematic linkages, hydraulic mechanisms, electrical solenoid mechanisms, screw mechanisms, magnetic linkages, or any combination thereof. In some embodiments the separated parts of the warming block are automatically closed upon insertion of the sample vial into the warming block sample vial receiver well to efficiently contact the sample container on all or most of the lateral surfaces of the sample container.

In some embodiments the invention will provide audio or visual feedback to allow the user to be informed of the device state and the status of the sample thawing process. In some embodiments, upon reaching the desired end-point of the melting process, the invention will alert the user using a visual and audio signal.

In some embodiments, the invention will be dedicated to a general type and shape of sample vial with no available user input other than selection of an on-off state. In other embodiments, the invention will accept input from the user. In some embodiments, the predictive thawing model may, without limitation, be adjusted by user input to account for the type of the sample container holding the sample, presence of a label on the sample container, a sample container fill level, and/or age of the thermally conductive medium between the warming block and the vessel.

Optionally, the system may provide an alert to a user when the melting sample reaches a desired level of remaining solid phase. In some embodiments, the desired end-point is a state wherein solid phase is a small fraction of the starting amount of solid material. In other embodiments, the desired end-point of the thaw process may be when the solution is completely liquid. In some embodiments, the end-point alert provided by the system may be an audio or visual indicator or combination of audio and visual signals. In other embodiments, an end-point alert may be wirelessly transmitted to a remote receiver to summon an operator that may not be in visual or auditory range of the thawing device. In some embodiments the alert signals are terminated by the removal of the sample vial from the warming block. Optionally, the system may automatically disengage one or more heating surfaces from the container to automatically reduce the heating of the container. In some embodiments, the system may be configured to adjust one or more heating surfaces in contact with the container to maintain or hold the temperature of the sample at a specific temperature after the end of the thawing or at the desired end point.

In some aspects of the present invention, a method for thawing a sample in a sample container is provided. The method may include the step of heating a warming block and receiving the sample container within the warming block. Thereafter, temperature measurements may be taken from the sample container and/or of the sample. A trigger point may be determined for using a time interval value for the remainder of the process. For example, a thaw start time (e.g., start of phase change) may be the trigger point for starting a time interval that identifies the end of the thawing process. The thaw start time may be determined based on the temperature measurements. Information on the sample and/or sample container may be received. A thaw completion time may be determined in-part on the thaw start time. The thaw completion time may be adjusted per the received sample and/or sample container information. A signal may be provided for alerting a user to the thaw completion time.

As the prediction of the thawing duration may be greatly facilitated by depending only on a uniform starting temperature, a uniform warming block temperature, and a uniform sample vial configuration, in other aspects of the present invention, devices and methods for equilibrating a sample vial to a standard starting ultra-cold temperature way point while eliminating any direct contact of the sample vial with dry ice are provided. In some embodiments of the invention, an insulating container in which solid carbon dioxide or dry ice may be placed and upon which may be place or embedded a thermally conductive container for the sample vials is provided. In other aspects of the present invention, methods are provided for retrieving a cryogenically preserved sample specimen vial from cryogenic storage at cryogenic temperatures and re-equilibrating the sample vial to an ultra-cold standard temperature way point prior to initiation of the thawing process whereupon, following transfer of the equilibrated sample to a warm block of standard and uniform temperature, the duration of the thawing process may be predicted on the basis of a known time constant exclusively. In other aspects of the invention, methods are provide wherein the previously described method is applied, but also enhanced by additional thaw time prediction capabilities derived from computational analysis of sample vial external surface thermometric data.

In further embodiments of the present invention, a device may be provided for the conversion from a solid state to liquid state of a sample contained in a vessel. The device may include a pliable solid material forming a receptacle for receiving the vessel and a heater for heating the pliable solid material to a temperature higher than a melting point of the sample. The pliable solid material may be interposed between the vessel and a non-pliable solid material when the vessel is received within the receptacle formed by the pliable solid material. The non-pliable solid material may comprise a material with a thermal conductivity between 10 Watts per meter-Kelvin and 410 Watts per meter-Kelvin, with a typical thermal conductivity between 100 and 300 Watts per meter-Kelvin, and in some embodiments a thermal conductivity between 150 and 180 Watts per meter-Kelvin. Materials with thermal conductivities in this range may exhibit a material hardness greater than a Shore durometer scale D value of 75 such that even when manufactured to close tolerances to mate with the vessel surface, minute air gaps may be present in the interface between the vessel and the solid receptacle, thereby introducing interruptions in the thermal conduction path across the material interface that may introduce a variance in thermal resistivity that is unpredictable in severity and frequency of occurrence. In addition, although the general shape and dimensions of cryogenic storage vessels may be similar, variation by manufacturing source is to be expected. Therefore, an interposition of a thin layer of compliant material between the sample vessel and the solid material receptacle can eliminate or substantially reduce the size and number of the air gaps and provide a uniform pathway through which thermal energy may be transferred from the solid material to the sample vessel contents. An example of a pliable material would include, without limitation, the thermally conductive pliable material sold commercially as Gap Pad VO soft by The Berquist Company, the material having a Shore OO hardness rating of 25 as determined by the ASTM D2240 test specification. As elimination of air gaps between a solid material receiver and the sample vessel wall may require only a thin layer of pliable material, a typical thickness, without limitation, of 0.5 mm to 2 mm may be sufficient to insure adequate thermal contact, however as pliable materials may exhibit thermal conductivities that are low when compared to solid materials, pliable materials with a thermal conductivity greater than 0.01 Watts per meter-Kelvin may be applied, while a typical pliable material may have a thermal conductivity greater than 0.1 Watts per meter-Kelvin, while in some embodiments the pliable material will have a thermal conductivity of greater than 0.5 Watts per meter-Kelvin.

The pliable material and the non-pliable material may be permanently bonded together. Optionally, the pliable material and the non-pliable material may be removably bonded together.

In some embodiments, the pliable and the non-pliable material may be segmented into two or more segments and the segments may be joined by a mechanical linkage that may move the segments into an open configuration for receiving or releasing the vessel and a closed configuration for forming the receptacle and thawing the vessel. The pliable material may be selectively placed in contact with the vessel when transitioning the segments from the open configuration to the closed configuration or removed from contact with the vessel when transitioning the segments from the closed configuration to the open configuration.

A vessel sensor may be provided for detecting the presence of the vessel between the segments of the pliable material when the segments are in the open configuration and closed configuration.

A micro-controller may be provided for controlling the mechanical linkage. When the segments are in the open configuration, the micro-controller may be configured to detect a placement of the vessel at a position between the segments while the segments are in the open configuration. The micro-controller may also be configured to deliver a control signal to actuate the mechanical linkage to move the segments toward the closed configuration to contact the vessel with the pliable material of the segments upon insertion of the vessel into the position between the open segments.

When the segments are in the closed configuration and thawing the vessel, the micro-controller may be configured to interrupt thawing of the vessel by delivering a control signal to actuate the mechanical linkage to move the segments toward the open configuration such that the pliable material of the segments do not contact the vessel.

In some embodiments, the non-pliable material may be heated by the heater.

A temperature sensor may be provided and may be fixed in the non-pliable solid. The temperature sensor may be thermally insulated from the non-pliable solid and may be held in contact with the vessel at a contact location such that a temperature signal reported by the temperature sensor may be associated with a temperature of an exterior surface of the vessel at the contact location.

In some embodiments, the start of the phase change of a thawing sample may be determined by algorithmic analysis of the temperature data from one or more of the temperature sensors operably coupled with the vessel at a location below the top level of the sample contained therein.

The heating of the pliable material may cause radial heating of the vessel to achieve a thaw time that is predominantly independent of a vessel fill level.

In further embodiments of the present invention, a method of thawing sample within a vessel may be provided. The method may include receiving a temperature data feed from a temperature sensor operably coupled with the vessel (e.g., in direct contact with an exterior surface of the vessel at a location along the exterior surface of the vessel that is below a top level of the sample within the vessel, an infrared temperature sensor, or the like), and identifying a start of a solid to liquid phase change of the sample contained in the vessel by processing the temperature data feed. A thaw end time may be calculated based on the start of the solid to liquid phase change of the sample contained in the vessel. A signal may be outputted to interrupt thawing of the sample contained in the vessel at the calculated thaw time.

In further embodiments, another method of thawing a sample within a vessel may be provided. The method may include equilibrating the sample and vessel to an intermediate temperature. The intermediate temperature may be below a sample melting temperature. Thereafter, the sides of the vessel may be contacted with a solid material mass that is maintained at a thawing temperature. The thawing temperature may be greater than 5 degrees above the melting temperature of the sample plus or minus two degrees. A thaw rate that is as rapid as possible may be desired to minimize the damage from ice recrystallization during the thaw process. A reduction in the thaw interval is favored by an increase in the temperature of the vessel receptacle, however as certain vessel shapes such as cylindrical formats may be associated with solid sample thicknesses greater than 1 centimeter in diameter, melting of solid materials contained therein will be accompanied by temperature gradients with a higher temperature at the vessel interior wall, decreasing in magnitude to the solid material remnant temperature toward the center. While liquid sample temperature transients due to temperature gradients incurred by a 37° C. bath thaw of a standard 1.8 ml cryogenic vial do not seem to impact the viability of the majority of established cell lines, the data set is not comprehensive and not reliably applicable to fresh cell isolates and primary cultures, and unfavorable results have been observed for some cryopreservation fluids at temperatures as low as 5° C. Therefore, the optimal thawing rate for a given cell source or viral stock may be case specific, however receptacle temperatures are expected to range from −1° C. to 100° C., typically from 20° C. to 55° C., and in some embodiments, 37° C. to 50° C. A completion of a phase change of the sample contained in the vessel may be predicted by calculating a time interval for a duration of the phase change based on the equilibrating temperature and the heating temperature. A signal may be outputted to interrupt thawing of the sample contained in the vessel at the predicted completion of the phase change of the sample contained in the vessel.

The intermediate temperature may be between −78° C. to −70° C. The sample may be equilibrated to the intermediate temperature range by placing the sample vessel into a receiving container that is in contact with solid carbon dioxide. The receiving container and the solid carbon dioxide may be surrounded on sides and a bottom by insulation. In some embodiments, the insulation comprises a polymer foam material including, but not limited to polyethylene foam, polyurethane foam, polyvinyl foam, polystyrene foam, and combination blends thereof. In some embodiments, the insulation comprises foam material exclusively while in other embodiments, the insulation comprises a hard interior and exterior shell filled with a reaction-in-mold foam such as polyurethane. In other embodiments, the insulation comprises a stainless steel vacuum canister In some embodiments, the intermediate temperature may be between −196 to −180 degrees Celsius. The sample may be equilibrated to the intermediate temperature by placing the sample vessel into a receiving container that is in direct contact with liquid nitrogen. The receiving container and the liquid nitrogen may be surrounded on sides and a bottom by insulation.

In some embodiments, the method may further include receiving a data feed from a temperature sensor that is held in contact with an exterior surface of the vessel such that a temperature signal reported by the temperature sensor is associated with a temperature of the exterior surface of the vessel, while in other embodiments the temperature signal is reported by an infra-red sensor that is not in direct contact with the sample vessel and is receiving infra-red emission signals from the vessel contents through an optically-transmissive vessel wall or from the vessel wall directly. The calculated time interval for the phase change duration may be adjusted based on the received temperature sensor data feed.

The invention will be better understood on reading the following description and examining the figures that accompany it. These figures are provided by way of illustration only and are in no way limiting on the invention.

BRIEF DESCRIPTION OF THE DRAWINGS

FIG. 9 part B shows a graphic display of temperature data collected with a thermocouple located at the same depth as part A in an orientation parallel to the central axis of the sample vial near the interior wall of the same vial used to generate the data in part A.

DETAILED DESCRIPTION

Figure 1A:
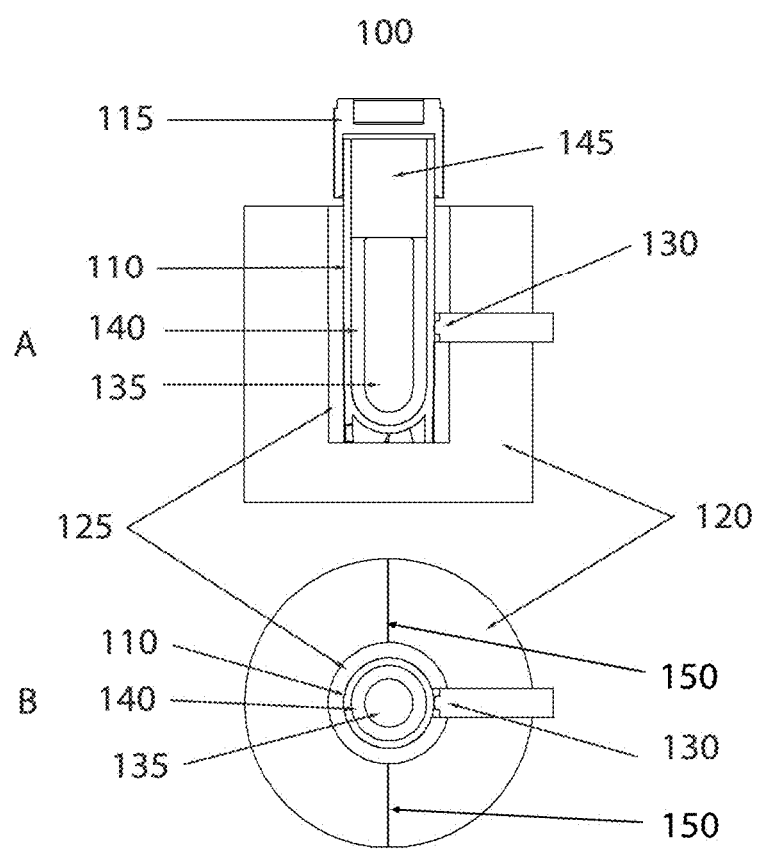
FIG. 1A shows a model thawing system for a typical cryogenic storage vial that is use in describing the thermal energy flow pattern and vial temperature detection methods.

The subject matter of embodiments of the present invention is described here with specificity, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

In some embodiments of the invention, direct liquid contact with the sample vial exterior may be eliminated, as would occur with a partial submersion of the sample in a water bath. As such, in many embodiments of the invention the exterior surface of the sample vial, or in some cases the sample vial exterior plus laminations such as labels or shrink-wrap sleeves, will be in contact only with solid materials. In some embodiments the solid material in contact with the vial exterior is a homogenous solid, while in other cases, the solid material is a complex material. In some embodiments, the solid material has a thermal conductivity of greater than 0.2 watts per meter-kelvin. In some embodiments the solid material comprises aluminum, copper, zinc, magnesium, titanium, iron, chromium, nickel, carbon, and alloys of the same elements. In some embodiments, the solid material may comprise a synthetic material such as a polymer or ceramic. In other embodiments, the solid material may comprise a synthetic thermally-conductive pliable material such as, but without limitation, the silicone polymer foam provided by The Berquist Company under the brand name Gap Pad VO. In some embodiments the solid material comprises combinations of materials, for example and without limitation, a conductive pliable material and a metal alloy. In some embodiments the solid material in contact with the sample vial exterior is a polymer shell or tank containing a liquid filling while in other embodiment, the solid material comprises a polymer shell or tank containing a liquid filling that comprises a thermally conductive lining of pliable material that contacts the sample vial contained therein. In some embodiments the liquid in the polymer shell is water or aqueous solutions while in other embodiments the liquid is an oil or a liquid organic material. In other embodiments the shell is filled with a wax that is liquid at some temperatures while solid at other temperatures.

In some embodiments, the sample vial or a portion of the sample vial is in continuous contact with the solid material on the circumference of the vial while in other embodiments, the solid material contacts the vial intermittently. In some embodiments, the solid material comprises a recess or cavity which closely matches the outer surface of the sample vial for the purpose of receiving the sample vial such that the sample vial is partially contained within the solid material in direct and close contact. In some embodiments, the container cavity comprises one or more sides and a floor, while in other embodiments, the container comprises only one or more sides. In other embodiments, the solid material containing the sample vial is segmented to facilitate the insertion and removal of the sample vial from the material and to interrupt the thermal conduction pathway between the solid material and the sample vial. In some embodiments, the solid material segments of the container are relationally constrained such that when separated to facilitate insertion or removal of the sample vial or to interrupt the thermal conduction between the solid material segments and the sample vial, the segments can be easily reassembled into a closely joined configuration. Without limitations, in some embodiments, the segments are joined by slide mechanisms, hinge mechanisms, track mechanisms, hydraulic or pneumatic pistons, rails, kinematic linkages, pin and groove linkages, electro-magnetic, or magnetic interface. In other embodiments, the segments are, without limitations, actively separated or joined by electric motors, solenoid activators, pneumatic or hydraulic actuators, linear actuators, either directly acting on the segments or by gear systems, kinematic linkages, cam systems, pushrods, cable system, and screw mechanisms.

In some embodiments, the solid material container for the sample vial comprises one or more heater elements for the purpose of increasing the temperature of the solid material such that when a sample vial is placed into the receiving cavity, thermal energy will migrate into the sample vial (from here forward referred to as "warming blocks"). In some warming blocks the heater elements are electrically resistive heaters while in other warming blocks, the heater elements are thermoelectric element heaters. In some embodiments, the warming block may be alternatively heated and cooled by a thermoelectric element. In some embodiments, the warming block comprises one or more temperature sensors that can detect the temperature of the block and provide an analog or digital signal to a microcontroller that is configured to interpret the thermometric signal and thereby regulate the power level or duty cycle supplied to the heater element in order to maintain the temperature of the warming block at the desired temperature.

In some embodiments, the warming block comprises one or more temperature sensors that are thermally isolated from the warming block material but are in contact with the exterior surface of the sample vial such that the temperature of the vial at the surface may be ascertained and tracked over time (from here forward referred to as the "vial sensor"). In some embodiments the vial sensor is a thermocouple while in other embodiments, the vial sensor is a thermistor or an RTD sensor. In other embodiments, the vial temperature is sensed by a non-contact infra-red sensor.

When a cylindrical sample vial that has been equilibrated to a low temperature, for example and without limitation, −77° C., is inserted into a warming block that has been equilibrated to a higher temperature, for example 45° C., a process of thermal energy redistribution will commence that will eventually bring the combined masses to a common temperature. If the warming block temperature is actively maintained, for example at 45° C., then the temperature of the combined masses will in time equilibrate at a temperature of 45° C. The thermal energy redistribution pattern may be considered to be a migration or flow of thermal energy in a radial pattern toward the central axis of the combined mass.

Now referring to FIG. 1A part A, a front cross-section view, and B, a top cross-section view, a representative model of a warming block 100 is shown. In this figure, an aluminum alloy cylindrical container 120 comprises a central cavity wherein a lining of thermally conductive pliable material 125 surrounds the vertical wall of the cavity except where an opening allows a thermistor temperature sensor 130 to protrude into the cavity. In this figure, the cavity is occupied by a sample vial tube 110 that is sealed with a screw cap 115 the combination of which isolates the sample contents comprised of a liquid phase 140 and a solid phase 135. The vial interior also comprises a gas phase volume 145. The thermometric sensor 130 is in direct contact with the exterior surface of the sample vial tube such that the temperature measured is the temperature of the exterior surface of the vial. Segmentation lines 150 bisect the aluminum alloy container and the thermally conductive pliable material. The aggregate of the components shown in FIG. 1A may be considered collectively to represent a system in reference to the thermodynamic illustrations to follow.

Figure 1B:
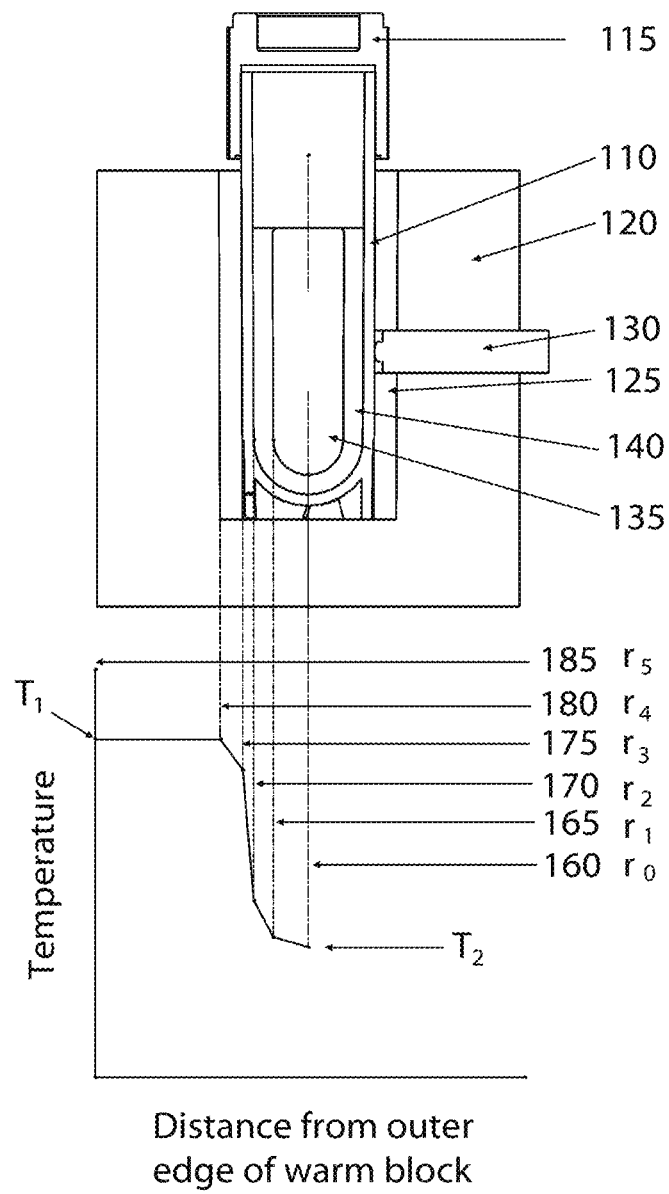
FIG. 1B shows a conceptualized graphic of the temperature decrease from the warming block temperature to the solid sample phase under a condition of dynamic thermal energy flow.

FIG. 1B shows the same graphic A as in FIGS. 1A and 1s used to mark specific material boundaries at the indicated radii. The boundary lines 180 to 185 define a region comprised of the aluminum alloy, lines 175 to 180 define a region comprised of thermally conductive pliable material, lines 170 to 175 define a region comprised of sample vial material such a polypropylene, polyethylene, or blends of polypropylene, polyethylene and additional plastic materials, lines 165 to 170 define a region of liquid sample phase, and lines 160 to 165 define a region of solid sample phase. As the model shown contains both liquid and solid phase, the state of the sample shown is during the melting or phase transition process. When the system shown is in the process of thermal energy redistribution, dynamic temperature gradients are established within the various materials such that the temperatures at the various material boundaries become dependent on the thermal resistivity of the materials. As represented in FIG. 1B, part B, the temperature with in the aluminum material is nearly uniform due to the low thermal resistance or high thermal conductivity (approximately 170 W/m-K) of the material. With the dynamic heat flow, however, a temperature drop is established across the region occupied by the thermally conductive pliable material (175 to 180) due to the relatively higher thermal resistance or relatively low thermal conductivity of the pliable material (approximately 0.8 W/m-K). A greater relative temperature drop will occur crossing the vial wall material (170 to 175) which has the greatest thermal resistance or lowest thermal conductivity of the system (approximately 0.2 W/m-K). Crossing the liquid sample material (165 to 170) a more shallow temperature drop will occur as the thermal resistance is similar in value to that of the thermally conductive foam (thermal conductivity of approximately 0.6 W/m-K), and the temperature drop across the solid sample material will be more shallow due to the lower thermal resistance when compared to the liquid phase (thermal conductivity of approximately 2 w/m-K). As the magnitude of the temperature decrease across the various materials increases with the magnitude of the difference in the warming block temperature ($T_1$) and the sample temperature ($T_2$), the temperature decreases across the various materials will be greatest in magnitude shortly after the sample vial is first inserted into the warming block and least in magnitude as the system approaches an equilibrium temperature. At any given time during the period of thermal energy migration, the relative temperature decreases across the various materials comprising the system will be a function of the thermal resistance of the various materials, the value of which does not change throughout the process, therefore the temperature at any one of the material boundaries can be considered to be proportional to the temperature at the other material boundaries, with the exception of the liquid-solid phase 165 ($r_1$) which will be subject to movement throughout the phase transition thereby changing the radius value and temperature depending on the location of the boundary in the system. Therefore a time-temperature trace at the conductive pliable material boundary 175 ($r_3$) can be an accurate proportional representation of the time-temperature trace at the vial wall-liquid boundary and a close approximation of the average temperature of the liquid phase. Therefore, by monitoring the external vial temperature during the thawing process, the time-temperature profile of the vial contents can be closely approximated, thereby allowing the progress of the sample thawing process to be determined non-invasively.

The amount of thermal energy required to raise the temperature of a sample vial and the contents from one temperature to a second temperature is dependent only on the heat capacity of the sample vial and the sample mass contained therein. Therefore if the material masses and the hence the amount of heat required to achieve the temperature transition do not change, and the start temperature of the warmer block and the start temperature of the sample vial are consistent, the same time temperature profile may be expected upon repeated freeze-thaw cycles of the same sample. If the sample vial dimensions, vial materials and mass, and sample payload mass and composition are uniform from sample to sample, the time-temperature profiles obtained should be identical regardless of whether the same sample is repeatedly cycled through a freeze-thaw or another sample is subjected to the same process. Therefore, the inclusion of a step or device for equilibrating all samples to a uniform starting temperature, and an accurate and uniform warming block temperature will allow the prediction of the thawing process duration to be made exclusively on the basis of prior experience.

Figure 1C:
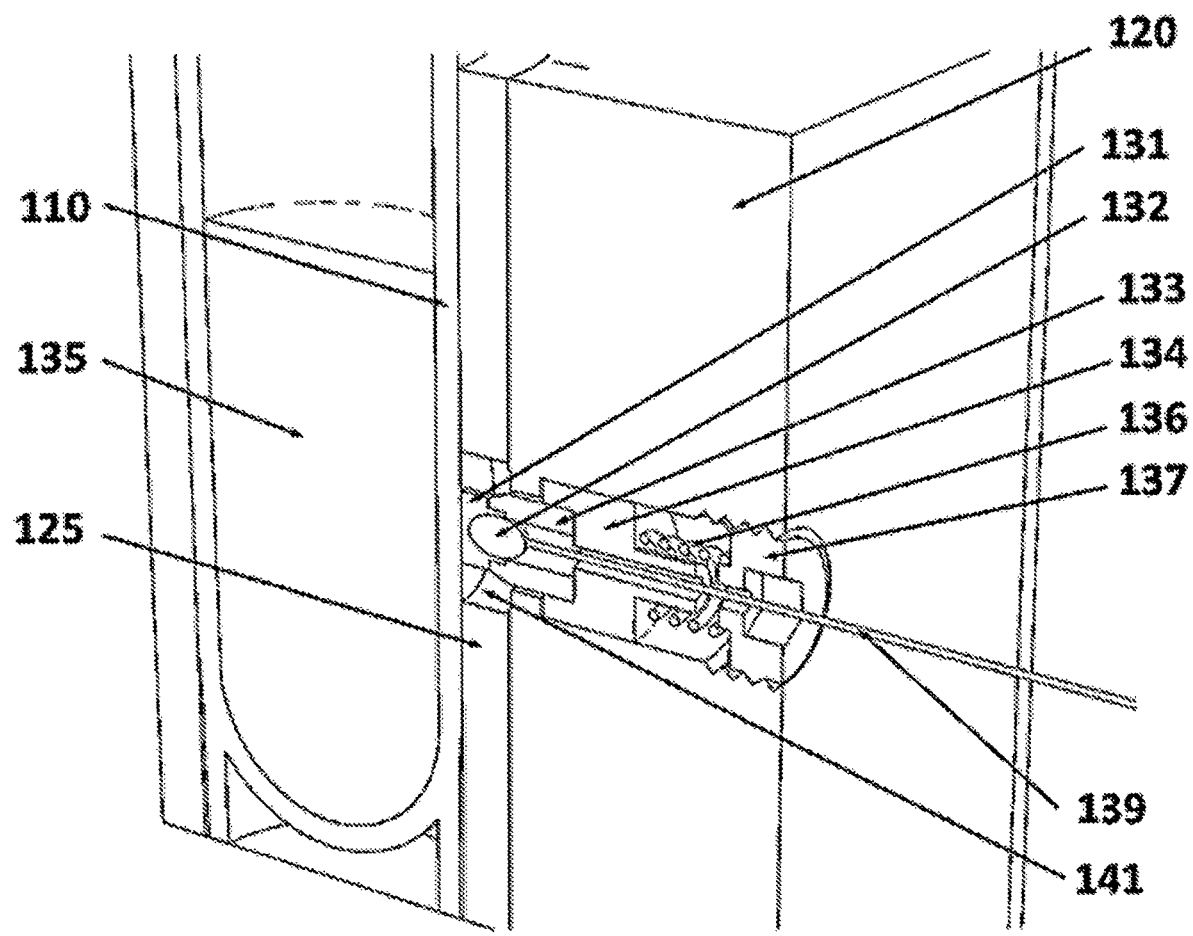
FIG. 1C shows a cross-section perspective of an embodiment of a vial surface temperature detection system.

Now referring to FIG. 1C, a detailed cross-section of an embodiment of the sample vessel surface temperature sensor (130 in FIGS. 1A and 1B) is shown. In this figure, a glass-encased thermistor bulb 132 is in direct contact with a thermally conductive coupler 131. In some embodiments, the coupler comprises a highly conductive material such as, but not limited to, aluminum, silver, copper or alloys comprising aluminum, silver or copper. The coupler 131 is in direct contact with the outside surface of the sample vessel wall 110. A semi-rigid foam insulator sleeve 133 holds the coupler 131 against the vessel surface, and is held under compression by a ram piston 134 that comprises an insulating material. In some embodiments the ram material is, without limitation, an acetal or phenolic polymer. The ram piston is placed under compression by a spring 136 that is captured between the sliding ram 134 and a screw plug 137 that is fixed in a threaded access hole through the warming block. A through hole in the screw plug 137 allows the passage of the thermistor lead wires 139 to the exterior of the block. A gap in the conductive foam 125 allows direct contact between the coupler 131 and the vessel wall 110 and limits direct thermal energy influx from the warming block 120. The thermal energy path created from the warming block 120 through ram piston 134, insulating sleeve 133 and coupler 131 to the vessel wall 110 creates a thermal resistance stack such that by selection of thermally resistive materials for the piston 134 and sleeve 133 and a thermally conductive material for the coupler 131, the temperature of the coupler, and hence the thermistor bulb 132, is closely coupled to the temperature of the vessel exterior surface 110 and therefore the temperature reported by the thermistor closely follows the temperature of the vessel surface. In some embodiments a thin layer of a pliable material (not shown), with an approximate thickness between 0.005 inches and 0.04 inches may be bonded to the coupler 131 and interposed between the coupler 131 and the vessel wall 110 to augment thermal conduction. In other embodiments, the thermistor assembly (131, 132, 133, 134, 136, 137, 139) is replaced by an infra-red thermal sensor. As materials used in the construction of cryogenic vessels may comprise materials that are optically transparent to infra-red light, the temperature of the vessel contents may be measured directly by infra-red emission. Where the vessel material is optically opaque to infra-red light, or the vessel may comprise an optically opaque label, the surface temperature may be measured by an infra-red sensor and the progression of the phase change from solid to liquid may be detected. The infra-red sensor has additional advantages in that physical contact between the sensor and the vessel is not required and therefore potential problems associated with sensor pressure on the vessel wall, variance in thermal conduction in the thermal sensing pathway, and potential sensor damage due to improper insertion of a sample vessel are eliminated.

Figure 2:
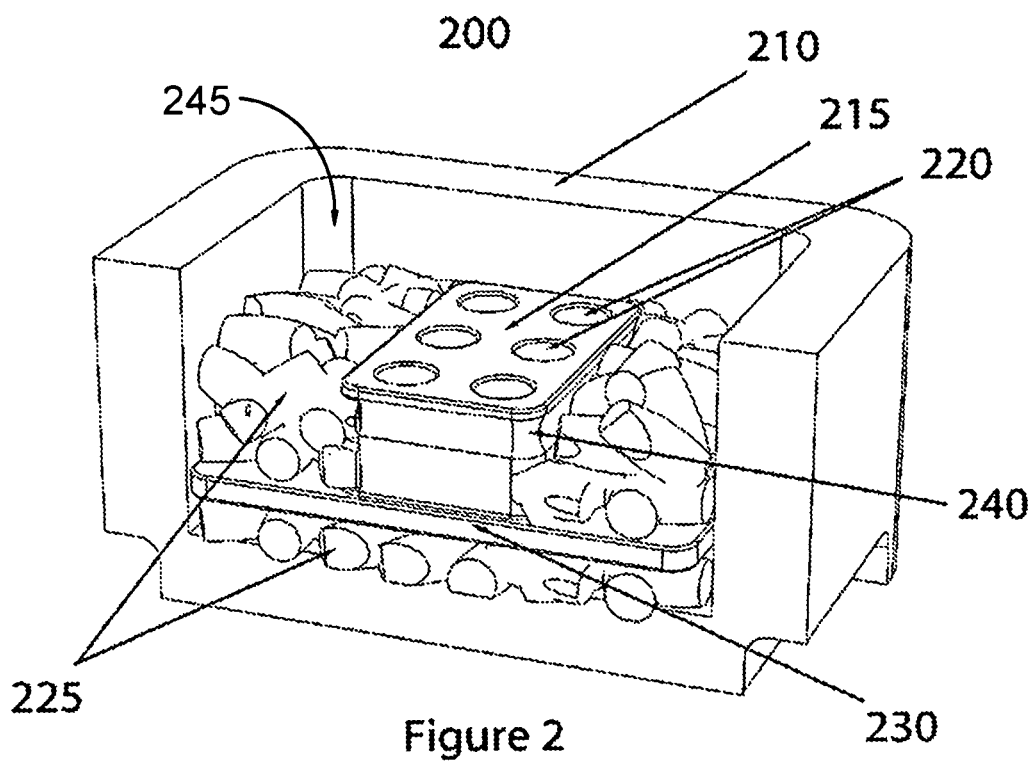
FIG. 2 shows an embodiment of a vial temperature equilibration device with dry ice refrigerant that equilibrates a vial temperature to approximately −77° C.

Now referring to FIG. 2, a device 200 is shown that may be used to equilibrate sample vials to a reference temperature (or intermediate temperature). In the figure, a sample vial receiver comprises a rectangular upper block of solid material 215 and a horizontal flange 230 that is mated to upper block forming a sample receiver block. The upper block 215 comprises one or more recesses 220 that are sufficient diameter and depth to receive and surround the sample vial such that the top of the sample contained within the vial is below the top surface of the block. In some embodiments, the receiver block comprises one or more recesses on the sidewall of the upper block 240 to assist in the grip security of the invention. In some embodiments, the flange 230 and the upper block 215 interface as an uninterrupted continuum of the material from which the parts are made, while in other embodiment the upper block 215 and the flange 230 are separate pieces that are joined, without limitations, by mechanical fasteners, adhesive bonds, magnetic fasteners, or weldements. In some embodiments, the upper block comprises a hole (not shown) into which a thermometric sensor may be inserted and secured. In some embodiments, the sample receiver block is constructed from a metal. In some embodiments, the metal comprises aluminum, copper, magnesium, zinc, titanium, iron, chromium, nickel or alloys of these metal elements. In some embodiments, the receiver block is surrounded on the sides and bottom by an insulating container 210 that has a cavity 245 with an interior height that is greater than the height of the receiver block plus 1 inch. In some embodiments, the insulating container comprises an insulating foam material. In some embodiments the insulating foam material comprises polyethylene, polyurethane, or polystyrene, while in other embodiments, the insulating material comprises a blend of materials such as a polyethylene polymer blend. In some embodiments, the insulating container comprises a cover (not shown). The receiver block is positioned in the insulating container such that as layer of solid carbon dioxide or dry ice 225 is positioned under and above the lateral surface of the flange 230. Although solid carbon dioxide in contact with a surface that is above the temperature of $-78.5°$ C. will sublime, thereby forming a gap between the solid carbon dioxide and the surface and interrupting the direct contact thermal energy conduction pathway between the materials, in a gravitational field, the dry ice will remain in direct contact with the undersurface of the receiver block and the upper surface of the receiver block lateral flanges. In embodiments the receiver block, without limitation, comprises a solid material has a thermal conductivity greater than 16 W/m-K such as aluminum alloy. The receiver block shown in FIG. 2 will maintain a steady temperature of $-77°$ C. in an open-top configuration. As the interior walls of the container exceed the height of the receiver block by at least one inch, the amount of dry ice beneath the receiver block may be limited such that the entirety of a sample vial placed into a receiver well will be positioned below the top surface of the insulating container, thereby holding the sample in a well of cold gas, and insulating the upper portion of the vial from the environmental temperature. In this configuration, vial temperatures, as measured with an internal thermocouple can be equilibrated to and held at a reference temperature of $-77°$ C. As such, the reference temperature device shown in FIG. 2 can be used to provide a standard starting temperature for the sample thawing process that will allow the prediction of the thaw process status based exclusively on the duration of the thaw process.

Figure 3:
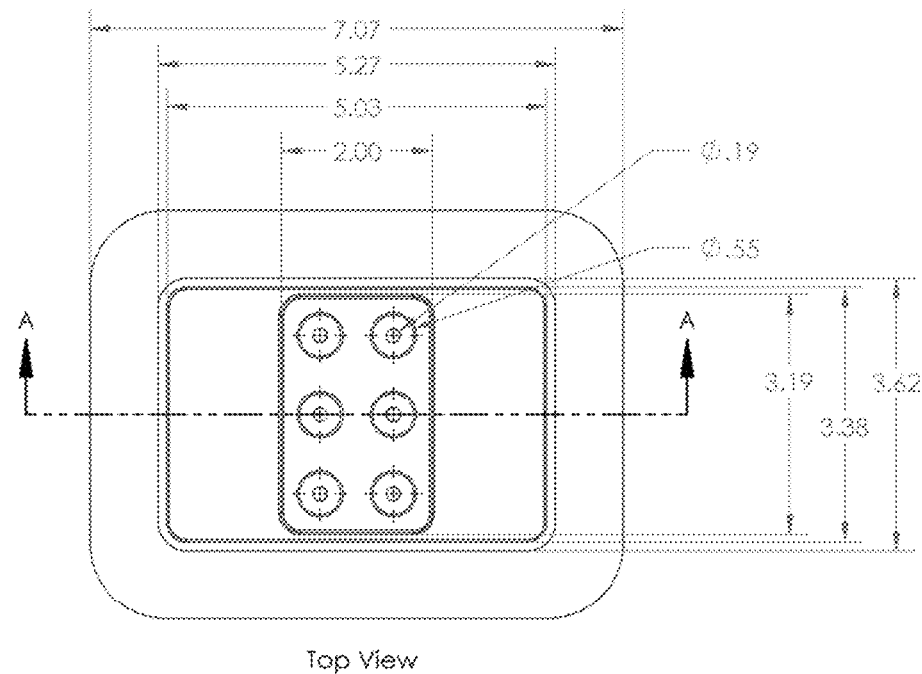
FIG. 3 shows a dimensioned drawing of the device described in FIG. 2.
Figure 3:
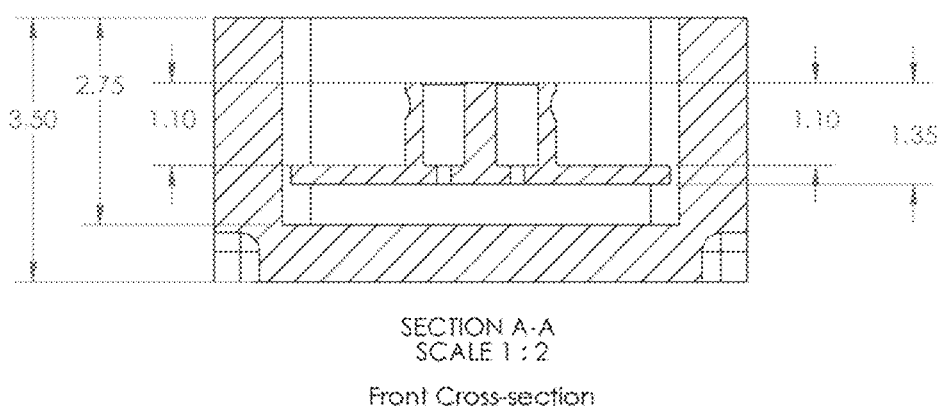

Now referring to FIG. 3, the overall dimensions of the device shown in FIG. 2 is shown. The embodiment has an outside width of approximately 7 inches, a width of approximately 5.5 inches and a depth of approximately 3.5 inches. The internal cavity has a length of approximately 5.25 inches, a width of approximately 3.6 inches, and a depth of approximately 2.8 inches. The receiver block has a length of approximately 5 inches, a width of approximately 3.4 inches and a height of approximately 1.35 inches. The sample vial receiver wells of the receiver block have a diameter of approximately 0.55 inches and a depth of approximately 1.1 inches. In some embodiments, the wells of the receiver block comprise a passage in the floor of the wells that extends to the undersurface of the receiver block so that the receiver block may be used efficiently with a liquid refrigerant such as liquid nitrogen. In FIG. 3 the passage way has a diameter of approximately 0.2 inches. Although the dimensions of the sample receiver wells shown are for receiving a standard laboratory screw-cap cryovial, the dimensions, spacing and number of the sample receiving wells may be adjusted to accommodate sample vials of other dimensions. In some embodiments, the diameter and depth of the wells may be adjusted to provide a go no-go gauge for the sample vial by which a user may determine if the vial intended for the thawing process is too large for the thawing apparatus or is too small to be used properly with the same.

Figure 4:
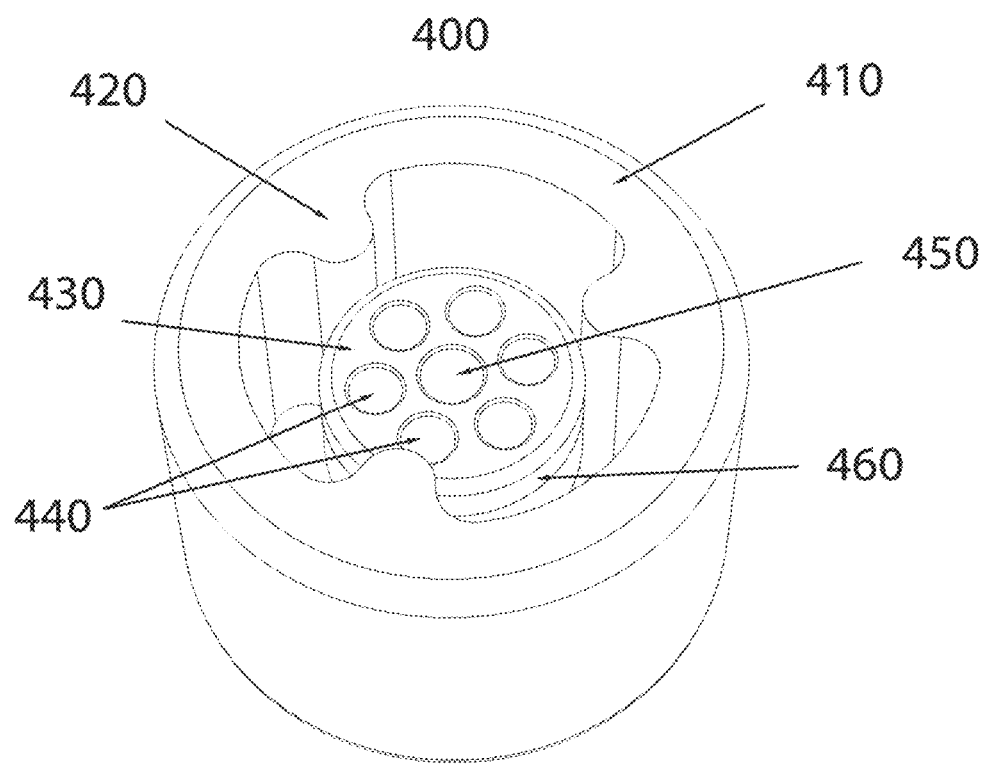
FIG. 4 shows a second embodiment of a vial temperature adjustment device.

Now referring to FIG. 4, a second embodiment of a temperature equilibration device 400 is shown. In this embodiment, a circular receiver block 430 is shown comprising a radial distribution of sample vial receiver wells 440. In some embodiments, the receiver block may comprise a central well 450 that may be provide an additional vial receiver well, be used as a through hole by which to assess the presence of dry ice beneath the receiver block, or provide a gauge for the purpose of confirming the appropriate vial dimensions that are compatible with the thawing device. The receiver block 430 is situated within the internal cavity of an insulating container 410. In some embodiments, the receiver block 430 comprises a hole into which a temperature sensor may be inserted and secured (not shown). In some embodiments, the insulating container 410 comprises internal extensions of the cavity wall 420 that support or limit the movement of the receiver block 430, while in other embodiments, the internal wall of the insulation housing 410 is a cylindrical shape without extensions. In some embodiments, the receiver block and the insulating container comprise the same materials described for the embodiments presented in FIGS. 2 and 3. In some embodiments, the receiver block 430 comprises a disc-shaped flange attached at the bottom surface of the receiver block (not shown) while in other embodiments the receiver block comprises the upper block 460 only.

Figure 5:
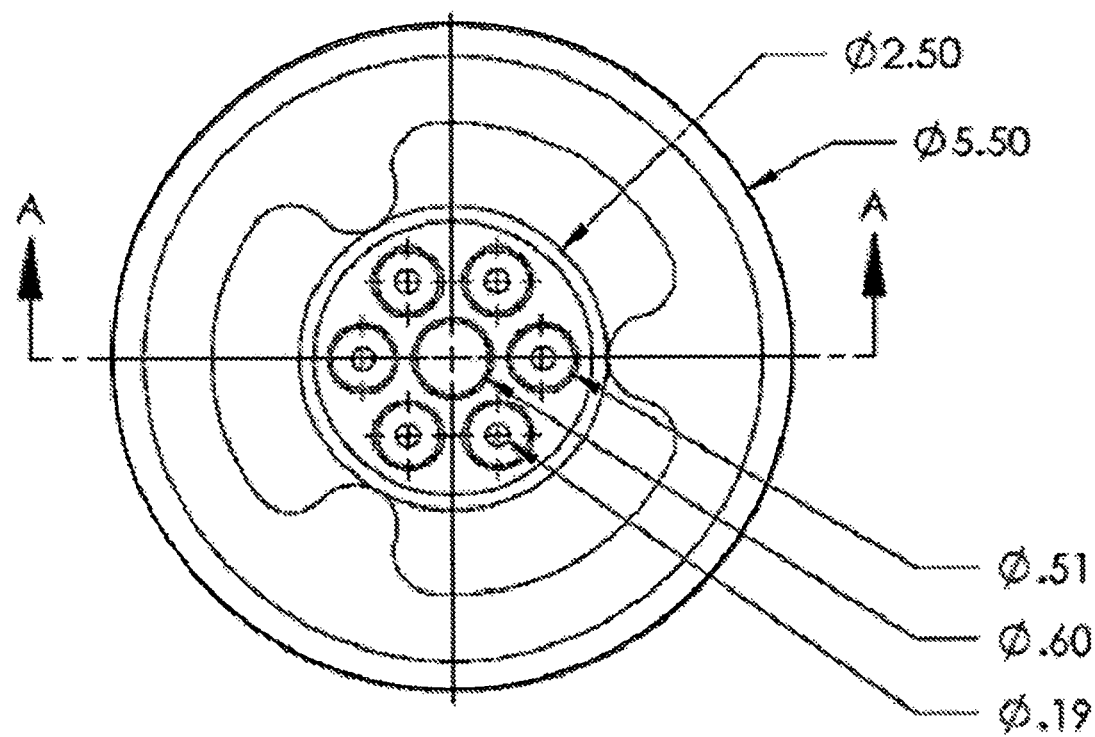
FIG. 5 shows a dimensioned drawing of the device described in FIG. 4.
Figure 5:
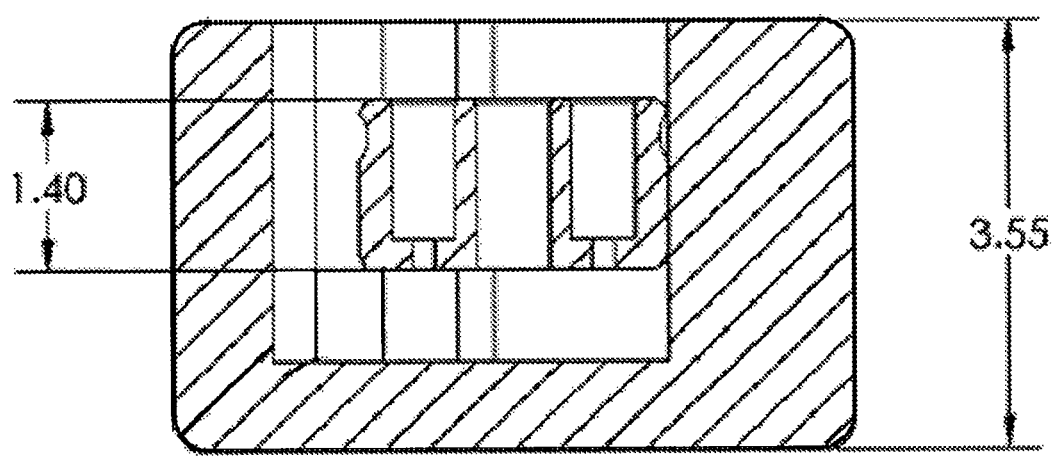

Now referring to FIG. 5, the overall dimensions of the device described in FIG. 4 are shown. The insulating container has an outside diameter of approximately 5.5 inches and a height of approximately 3.5 inches with an internal cavity diameter of approximately 2 inches and a depth of approximately 2.8 inches. The receiver block has an outside diameter of approximately 2.5 inches and a height of approximately 1.4 inches. The vial receiver wells of the receiver block have a diameter of approximately 0.51 inches and a depth of approximately 1.15 inches. The central cavity has a diameter of approximately 0.7 inches and in the embodiment shown extends through to the undersurface of the block. In some embodiments, the vial receiver wells of the receiver block comprise a passage extending through the floor of the well to allow flooding of the well when the receiver rack is used with a liquid refrigerant such as liquid nitrogen. In some embodiments the passage has a diameter of approximately 0.2 inches. In other embodiments, the sample vial receiver well floor is solid and does not comprise a passageway.

Figure 6:
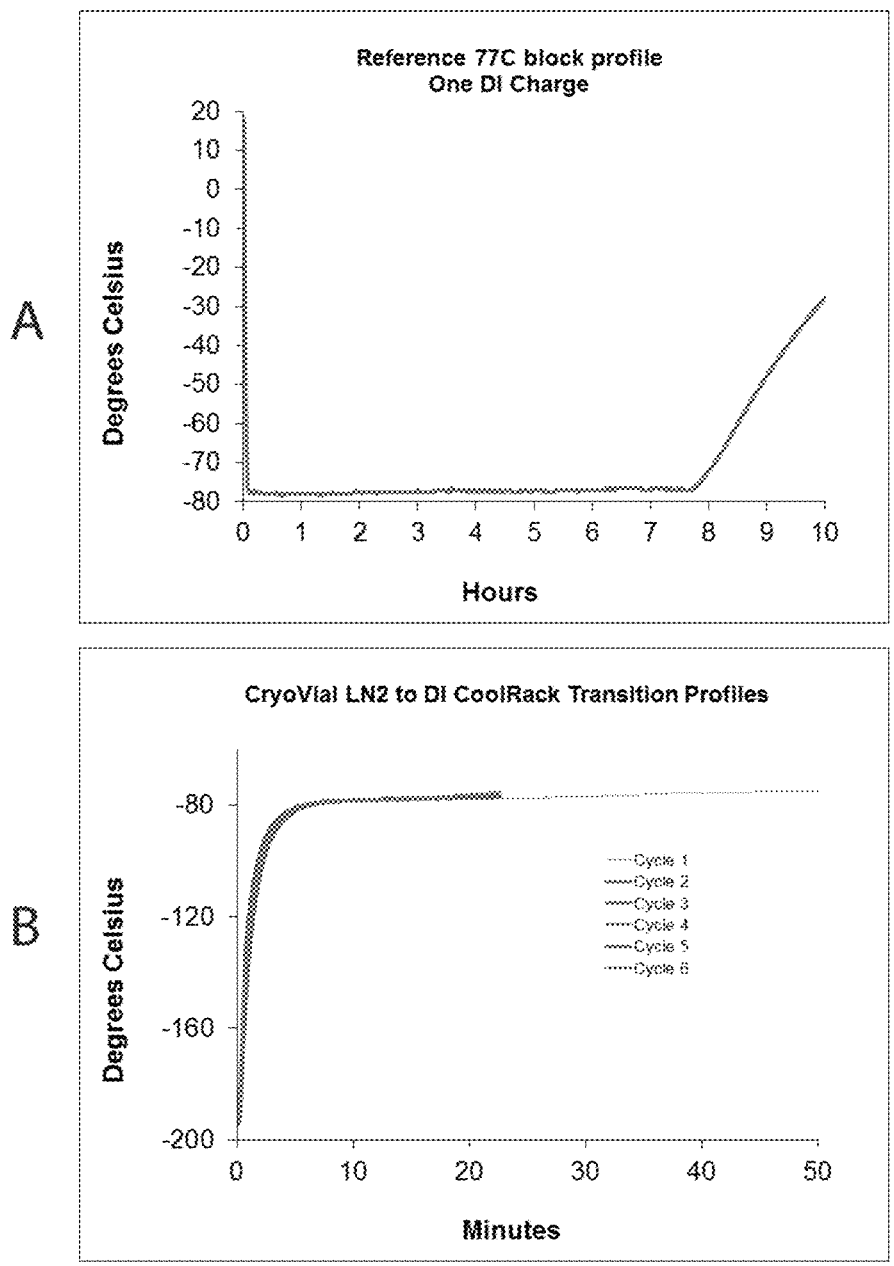
FIG. 6, graph A, shows a graphic display of the cooling and temperature-holding duration of the embodiment described in FIGS. 2 and 3. Graph B shows the uniformity in the temperature transition of sample vial contents when transferred from liquid nitrogen to the temperature-equilibrated device described in FIGS. 2 and 3.

Now referring to FIG. 6, part A, a data graph of the temperature of a receiver block as described in FIGS. 2 and 3 is shown. The temperature measurements were collected by a thermocouple sensor that was positioned into a receiver hole drilled into the vial receiver block to a depth of 0.5 inches. The receiver block was placed upon an approximately 0.75 inch thick layer of dry ice, and additional dry ice was placed over the flange portion of the receiver block to a level equal to the top of the receiver. The receiver was allowed to temperature equilibrate. As seen in the graph, the receiver block reached a temperature of −77° C. in approximately 5 minutes and held the temperature for over 7 hours until the dry ice was exhausted. During the 7-hour interval a sample vial containing 90 percent buffered saline and 10% dimethyl sulfoxide in a volume of 1 ml was configured with a thermocouple temperature sensor held in an axial orientation with the thermocouple sensor positioned mid-height in the sample liquid. The sample vial was then equilibrated to a temperature of −194° C. in liquid nitrogen, then transferred to the −77° C. equilibration block. As shown in part B of FIG. 6, the temperature of the vial contents equilibrated to the −77° C. temperature within an interval of approximately 10 minutes. Following repeated cycles of thawing, re-equilibration in liquid nitrogen and transfer to the −77° C. receiver block, the temperature profiles of the sample contents are highly repeatable. Using this simple equilibration device and method, a sample stored at cryogenic temperature may be retrieved from archival storage and be rapidly equilibrated to a steady temperature of −77° C. The sample may then be stored for an extended period of up to 7 hours or longer if the dry ice refrigerant is replenished. The receiver block at −77° C. provides a highly reproducible temperature start point for a thawing process, allowing the thaw time of a sample to be accurately predicted following placement into a warming block that has been equilibrated to the appropriate temperature. In addition, the receiver block prevents direct contact of the sample with the dry ice refrigerant. As some vial designs comprise a skirt extension on the undersurface (see FIG. 16, vial A), direct insertion of these vial into dry ice will capture dry ice in the underside recesses and if subsequently inserted into a warming block will experience a significant change in the thaw time due to the additional heat influx required to change the dry ice to the gas phase. Therefore the use of a receiver block that isolates the sample vials from direct contact with the dry ice is preferable for the standardization of the thawing process.

Figure 7:
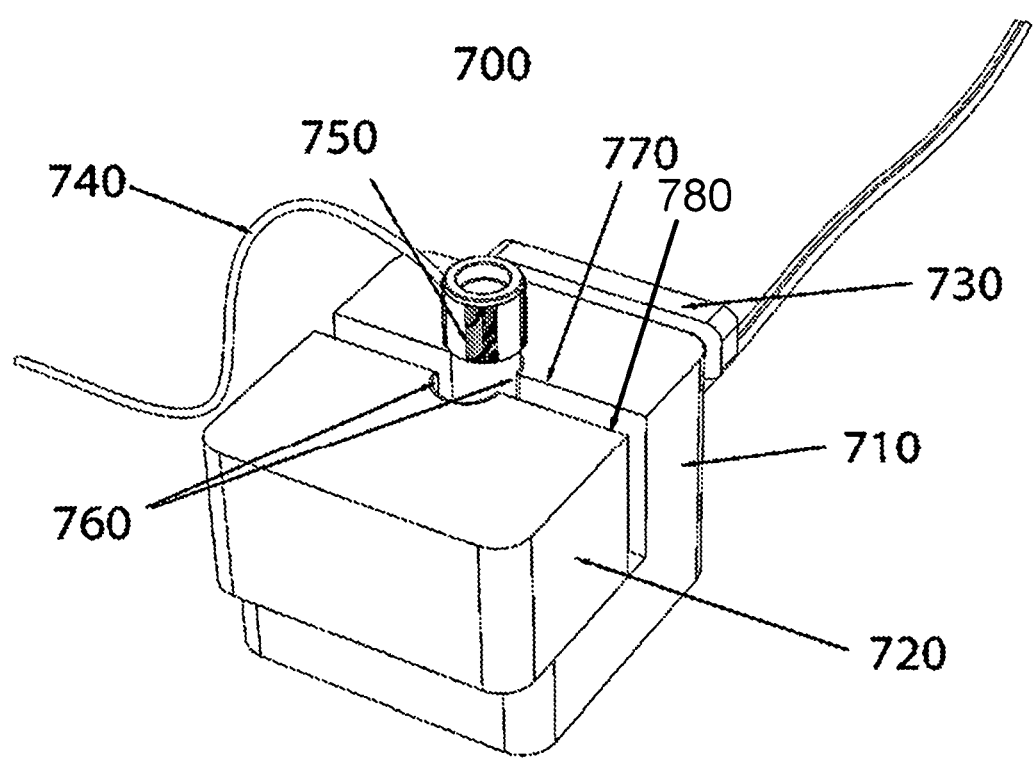
FIG. 7 shows an embodiment of a split-block vial thawing device.

Now referring to FIG. 7, a standard warming block assembly 700 is shown. In this embodiment, the warming block 710 is segmented by two right-angle planar interfaces 770 and 780 to create an independent block segment 720. The vertical segmentation plane passes through the center of a cylindrical sample vial receiving well coincident with the cylindrical axis of the receiving well. The receiving well shown comprises a 1-degree cylindrical taper to match the taper of a standard screw-capped cryovial 750 such as those available commercially from multiple vendors and being comprised of a material having a thermal conductivity of less than 2 Watts/meter-K including, but not limited to, polypropylene, polyethylene, or blends of polypropylene, polyethylene and additional plastic materials, plastic resins and resin blends, and glass. The receiving well walls comprise a 0.5 mm-thick layer of thermally conductive material such as, but not limited to, thermally conductive foam 760, with the innermost surface matched the surface of the standard screw-capped cryovial such that when the cryovial is placed into the well and the two receiver blocks close to near contact at the surface 770, the cryovial surface and the conductive foam are in close and complete contact at all points. The movable sliding segment 720 is confined to a linear horizontal motion by two push-rods (hidden in this perspective) that are secured at the end by a push-bar 730. By horizontal actuation of the push-bar, the segments of the warming block may be separated to allow insertion or removal of the cryovial. It may be noted that an embodiment that does not comprise the thermally conductive foam can be constructed, however, perfectly matching the taper of the cryovial is a difficult achievement and from manufacturer to manufacturer, variation in the angle of the taper and the diameter of the vial may be encountered. In addition, upon freezing, the aqueous contents of the sample vial will expand with the potential to distort the exterior surface of the cryovial. Further complications may arise in mating the receiver well surface to the vial exterior surface in that the vials may be unpredictably laminated with an identification label, therefore a compliant surface in the receiver well is essential to uniform, complete and repeatable contact of the two surfaces as any disruption in the physical contact will alter the thermal transfer by imposing additional thermal resistance at the location of the disruption. Therefore, the thermally-conductive and compliant interface 760 is preferred in some embodiments. The warming block 710 is heated by an electric resistance heater (hidden in this view) that is embedded in the undersurface and powered by an electrical current. The temperature of the warming block may be determined by a thermocouple sensor 740 is inserted into the warming block segment 710. The block segments 720 and 710 are further joined by embedded magnet pairs both on the vertical interface 770 and the horizontal interface, thereby assuring close thermal conductive contact of the two parts in addition to supplying clamping pressure to the inserted vial. The embodiment parts 710, 720 and 730 are constructed from an aluminum alloy. The thermally conductive foam lining is constructed from a thermally-conductive silicone composition sold commercially by Laird Technologies under Tflex brand.

Figure 8:
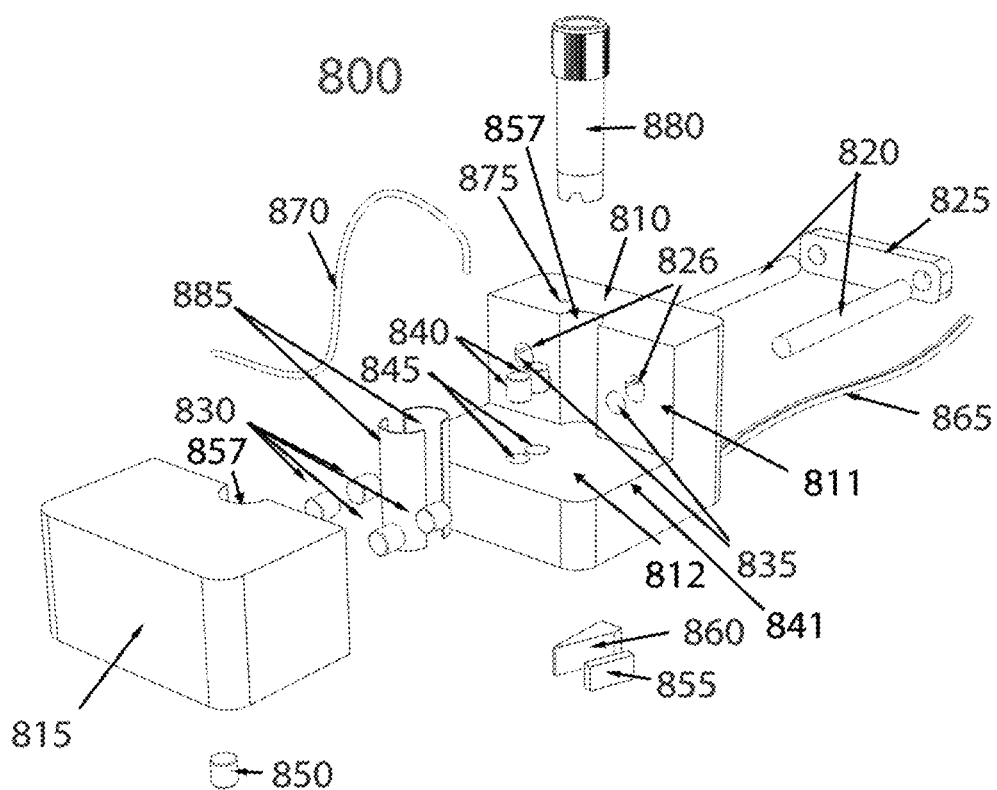
FIG. 8 shows an exploded view of the device shown in FIG. 7.

Now referring to FIG. 8, an exploded diagram of the embodiment shown in FIG. 7 is shown. In this diagram the L-shaped warming block 810 mates with a rectangular block 815 at two interface planes, 811 and 812. The two block segments are removably fastened on the vertical plane 811 by the interface of two magnet pairs 830 that are received in block 810 in the receiver cavities 835, and mirrored receiver holes on the rectangular block 815 (not visible in the view). On the horizontal plane 812, the two block segments 810 and 815 are joined by a single magnet pair in which one magnet 850 is embedded in the undersurface of block 815 while two separate opposing magnets 840 are embedded in the horizontal surface 812 in receiver holes 845. The single magnet 850 in sliding block 815 may selectively interface with either of the two magnets 840 by changing linear position along the axis defined by edge 841. The magnet 840 centers are spaced 0.28 inches apart and allow the block 815 to assume two stable positions, one being a position where the sliding block 815 is mated to block 810 at the 811 and 812 interfaces, and another where the two blocks are interfaced at plane 812 and with a gap of approximately 0.27 inches between the two vertical block faces, thereby establishing an open and closed warming block states. Two thermally pliant conductive material linings 885 are laminated onto the two inside wall halves of the vial receiver well 857. The block segments are warmed by a resistance heater 855 that is embedded into the underside of the block 810 in a wedge-shaped cavity and the heater element 855 is held in close thermal contact with the cavity walls by pressure from a wedge-shaped segment 860, the pressure on which may be adjusted by a force of a screw impinging on the back side of the wedge (not shown in this view). The heater is powered by an electrical current that is conducted through power wires 865. The temperature of the warming block may be monitored by the thermocouple sensor 870 inserted into the warming block 810 at the sensor receiver hole 875. The block 815 is supported laterally by two push-rods 820 that are bridged by a push bar 825 at the distal ends. The push rods extend through block 810 through access channels 826 which contact the push rods on the sides only and are machined in a vertical slot configuration to allow some degree vertical freedom such that the block 815 is supported exclusively by the horizontal surface 812 of the block 810. The warming block operates by manual separation of the block segments 810 and 815 by pressing on the push bar 825. A sample vial is inserted into the opened receiver cavity 857 and the jaws are closed by slight pressure on the block 815 until the magnet 850 separates from the proximal magnet 845 and re-aligns with the distal magnet 845 assisted by the added pull of the magnet pairs 830. In other embodiments, the warming block shown in FIG. 8 can be articulated and automated by active propulsion machinery including but not limited to motors, solenoid actuators, hydraulic and pneumatic actuators, and electro-magnets. The propulsion machinery may be linked to the block segments, without limitation, by screw machines, kinematic linkages, hinges, cables, belts, chains, pin and slot, tracks, rails, slides linear and rotational bearings, cams, and gears. In some embodiments, the system shown in FIG. 8 may comprise more than one temperature sensors by which the temperature of the warming block may be monitored. In some embodiments, the heater block comprises one or more temperature sensors that are thermally isolated from the warming block but are in contact with the surface of the sample vial. In some embodiments, the temperature sensors may comprise thermocouples, thermistors and RTD sensors. In other embodiments, the warming block comprises a microprocessor circuit board which receives warming block temperature feedback signals from the block sensors and regulates the power supplied to the heaters to maintain the desired block temperature. In other embodiments the microprocessor board receives position sensor data from proximity sensors on the warming block to determine when the block is open or closed. In other embodiments, the microprocessor board actively opens and closes the warming block according to a state algorithm that conducts the thawing process. In other embodiments, the microprocessor receives thermometric signal data from sensors in contact with the surface of the sample vial received into the warming block. In other embodiments, the microprocessor makes determinations of the thawing status of the vial by algorithmic interpretation of the thermometric data. In some embodiments, the microprocessor board controls a user interface that displays the status of the thawing process, alerts the users to fault conditions and signals the readiness of the warming block to receive a sample vial and initiate the thawing sequence.

In some embodiments, the size of the magnet pairs 830 and/or the field strength of the magnet pairs may be used to adjust the clamping pressure of the conductive pliant material linings 885 on the vessel 880, thereby changing the thermal conduction between linings and the vessel. In other embodiments the clamping pressure is provided by, without limitations, magnetic, electromagnetic, spring, pneumatic, hydraulic, or mechanical force, or any combination thereof.

Figure 9:
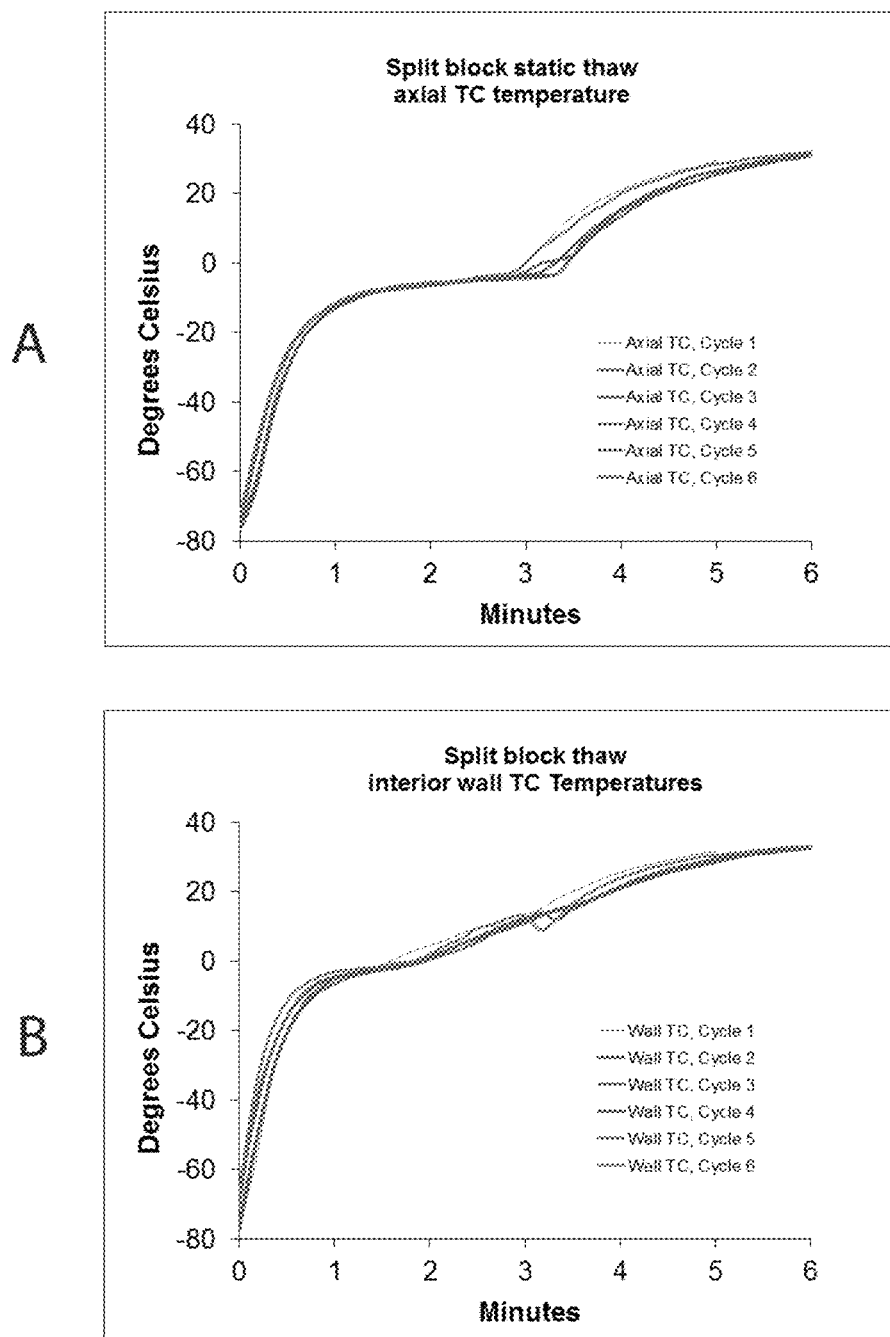
FIG. 9, part A shows a graphic display of temperature data collected with a thermocouple located in an orientation coincident with the central axis of the sample vial at mid-depth in the sample during multiple thawing events in the device described in FIGS. 7 and 8.

Now referring to FIG. 9, part A, a series of time-temperature traces are shown from a thermocouple sensor positioned internally in a sample vial along the central axis of the vial with the sensor bead at half-depth in a 1 ml sample comprising 90% buffered saline and 10% dimethyl sulfoxide. The vial was equilibrated to $-194°$ C. in liquid nitrogen, then placed into the equilibration device described in FIGS. 2 and 3 to equilibrate to $-77°$ C. for 10 minutes. The vial was then transferred to the warming block device described in FIGS. 7 and 8 that was pre-equilibrated to $37°$ C. for 6 minutes while a data recorder collected the temperature trace at 10-second intervals. The freeze thaw cycle was repeated 6 times and the time temperatures traces were plotted collectively. From the trace grouping, it can be seen that the thawing profile is highly repeatable until approximately 3 minutes. Near the three-minute mark, the central solid remnant of the sample is confined as the axial thermocouple is still embedded in the solid mass. As this solid remnant is released from the thermocouple sensor, the lower temperature solid is free to randomly separate from, contact, or intermittently contact the sensor, thereby introducing artifacts into the data stream. The repeatability of the data traces prior to the 3-minute point indicates that by starting at a consistent sample temperature, and using a regulated temperature warming block, the progress of the thawing process can be closely predicted using only experimentally-derived thaw interval time values. Therefore, in some embodiments a chronometric device, a temperature equilibration device as shown in FIGS. 2 through 5, and a constant temperature warm block as shown in FIGS. 7 and 8, are used to make an accurate prediction of the duration of the thaw process for a given sample vial. In other embodiments the reduction of the phase change completion time value by a constant will be used to terminate the thawing process while some solid phase is still remaining in the vial.

FIG. 9, part B shows a cluster of temperature traces from a thermocouple placed into the same sample vial such that the sensor lies near the interior wall of the vial. The traces reproduce those observed in FIG. 9, part A until approximately the one minute mark at which time the phase change begins. The temperature trace displays a higher trajectory that that observed in part A, indicating that the temperature near the inner wall is warmer than at the center of the sample load. This outcome is predicted by the complex thermal resistance pathway that the thermal energy must traverse as described in FIG. 1B. It is also noted that near the 3 minute time mark, artifacts in the temperature trace cluster are present, but with less severe deviation from the average temperature values than observed in FIG. 9, part A.

Figure 10:
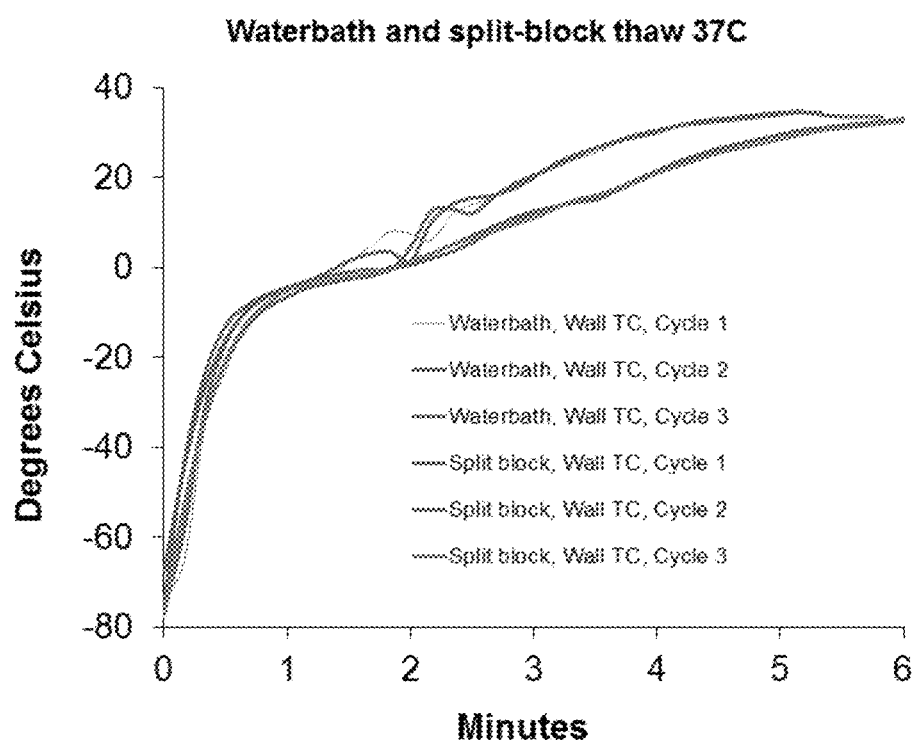
FIG. 10 shows a series of temperature change data profiles from a thermocouple positioned near the inner wall of a thawing vial as in FIG. 9, part B, when the vial is placed into a 37° C. water bath or placed into a warming block of the type described in FIGS. 7 and 8.

Now referring to FIG. 10, additional data was collected using the liquid nitrogen freezing and the −77° C. dry ice temperature equilibrium device used to collect the data in FIG. 9 with the thermocouple sensor situated in the same position used in FIG. 9 part B, near the interior wall of the vial. In the data shown, however one cluster of three cycles was collected using 37° C. warming block described in FIGS. 7 and 8, while the other cluster of three cycles was collected by partial submersion of the vial in a 37° C. water bath. Comparing the traces, it can be seen that the vials that were thawed in the warming block (indicated as the "split block" in the figure), are thawing at a slower rate. Again referring to the thermal energy flow model across a complex thermal resistance pathway as described in FIG. 1B, the result can be understood as there would be a temperature drop across the conductive foam material effectively placing the sample vial in a lower temperature environment than would be experienced by the same vial in a 37° C. water bath.

Figure 11:
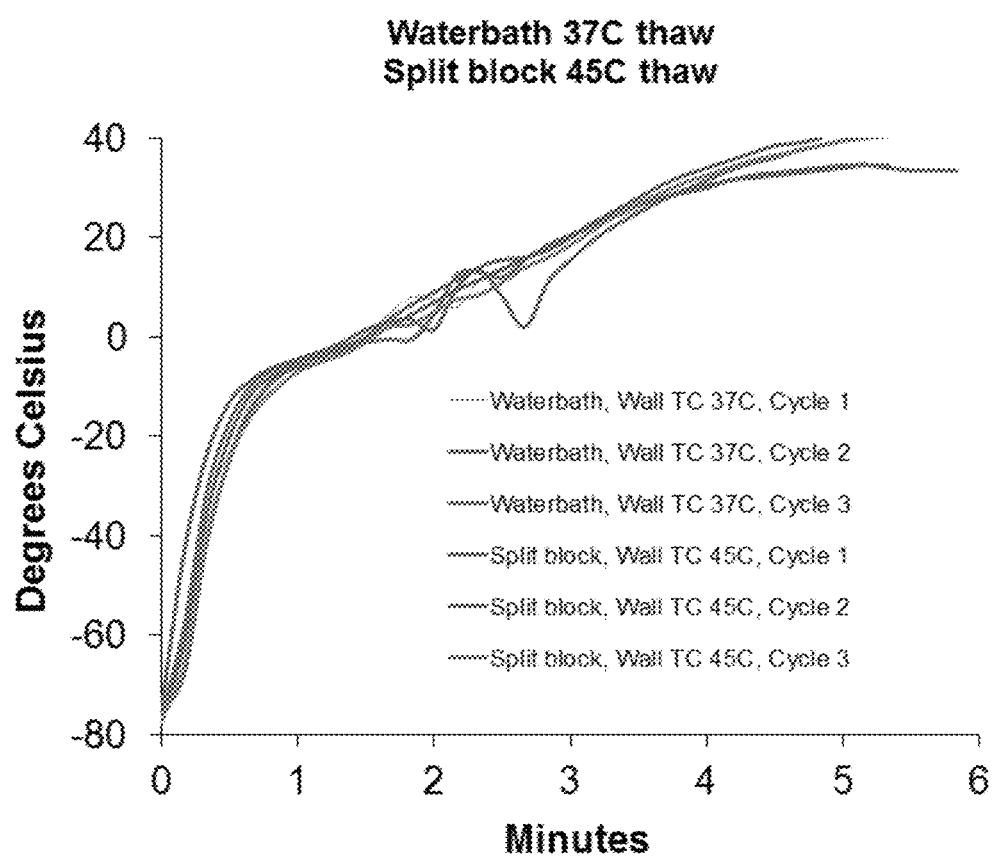
FIG. 11 shows an additional series of temperature change data profiles from a thermocouple positioned near the inner wall of a thawing vial when the vial is placed into a 37° C. water bath and into a 45° C. warming block of the type described in FIGS. 7 and 8.

Now referring to FIG. 11, the thawing series described in FIG. 10 was repeated using the identical systems with the exception that the temperature of the warm block or split block was equilibrated to 45° C. prior to beginning the thaw series. In the time-temperature graphs shown, the two trace clusters are overlaid indicating that by elevating the warm block temperature, the temperature at the conductive foam-sample vial interface can be elevated to 37° C., effectively creating a water bath-equivalent thaw using a solid warming block.

Figure 12:
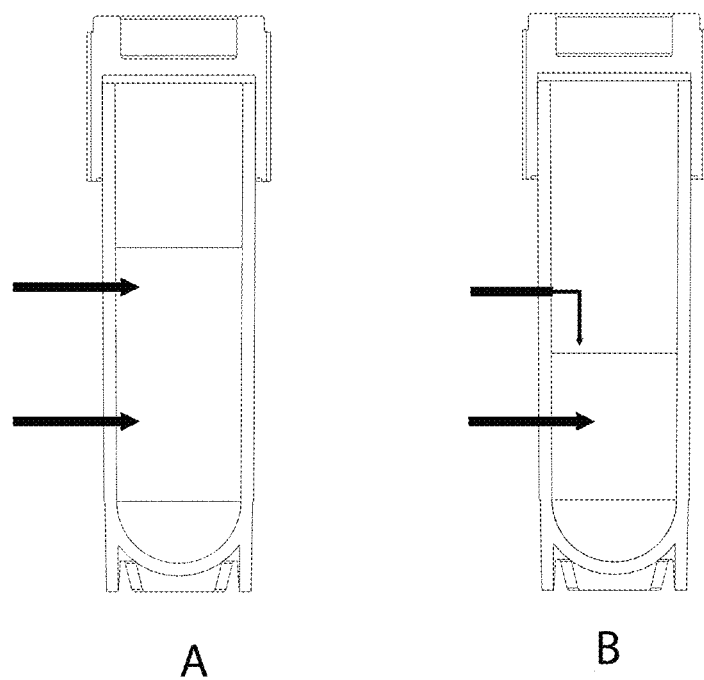
FIG. 12 shows a graphic representation of the heat conduction pathways and heat flow rates into a storage vial at two different levels of sample loading.

Now referring to FIG. 12 a cross-section diagram of two sample vials is shown to illustrate the load-volume independence of a thawing vial temperature trace for a cylindrical sample vial. In the vial A where the contents of the vial is greater, an identical thermal conduction pathway exists at the position of both of the arrows in that the inner wall of the vial is in direct contact with the sample. In vial B, the sample volume is reduced and therefore at the position of the upper arrow, the interior wall of the vial does not contact the sample, therefore thermal energy entering the vial at this location must either migrate downward through the thermally resistant polymer of the vial wall or migrate through the gas above the vial which has a thermal conductivity approximately one-tenth that of the polymer vessel wall. Therefore, the amount of heat entering the sample contained within the vial is proportional to the amount of sample in the vial. This effect is experimentally demonstrated in FIG. 13.

Figure 13:
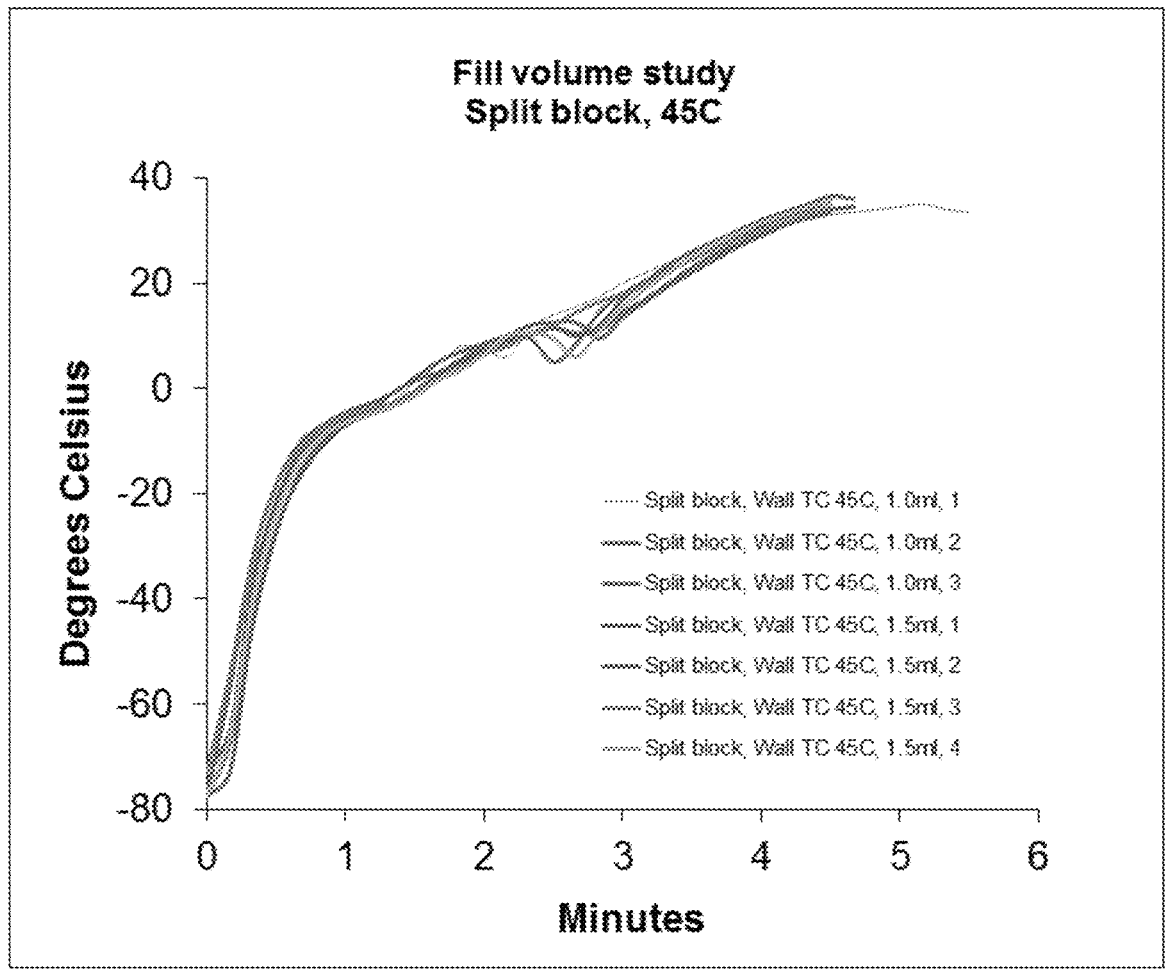
FIG. 13 shows a series of temperature change data profiles from a thermocouple positioned near the inner wall of a vial when the vial is placed into s 45° C. split warming block under conditions where the vial is filled with 0.5 ml of test solution and where the vial is filled with 1.0 ml of test solution.

Now referring to FIG. 13, temperature trace clusters were generated using the same warm block thawing system and method described in FIG. 11, with the exception that two different sample vial loads were used for the two thaw series. In one trace series the vials contained 1 ml of the test sample fluid and in the second series, the vials contained 1.5 ml of the test sample fluid. As can be seen in the time-temperature plots, the two series overlay indicating that the thaw profile is independent of the vial fill volume. It may be noted for the discussion of FIG. 14 that the beginning of the phase change occurs at approximately 50 seconds after the insertion of the vial into the warm block and that the end of the phase change occurs at approximately 160 seconds after the insertion of the vial into the warm block.

In the process of recovering viable biological samples from cryogenic storage, the optimal recovery of live cells is favored by rapid transition through the ultra-cold temperature region of −75° C. to the liquid state, as this practice will minimize the opportunity for injurious intra-cellular ice crystal grown to occur. While an increase in the bath or warming block temperature will decrease the duration of the temperature transition by increasing the rate of thermal energy influx into the sample vial, the experimental evidence shown in FIG. 9 demonstrates that during the thawing process, the temperature of a portion of the sample will experience temperatures higher than the phase-transition temperature of the sample. Although the temperature increase in regions of the sample due to the dynamic heat influx are transient, the toxicity of the cryoprotectants commonly included in the cryopreservation media for cell suspension cryopreservation increases with temperature, therefore reducing the thawing interval by increasing the bath or warm block temperature has associated risks for a portion of the sample. To reduce the exposure of the thawed sample to elevated temperatures, a common practice for sample thawing includes the cessation of exposure of the sample vial to the elevated temperature of the water bath at a time when a small portion of the solid sample still remains. This practice allows the still-solid remnant to absorb thermal energy from the liquid portion of the sample, thereby equilibrating the thawed sample to a low temperature. The accurate assessment or prediction of the nearly complete phase change state during the thawing process is therefore necessary. During manual thawing of a sample vial in a water bath, a common practice includes the frequent visual assessment the sample state. As this practice requires the removal of the sample from the water bath, variation in the duration of the thaw time is imposed as the thermal contact between the vial and the water bath heat source is frequently interrupted. Unless an alternative assessment of the sample state is applied, a repeated visual inspection of the sample would also require removal of the sample vial from a solid warming block as well, and under such conditions, a standardized thawing methodology could not be applicable. Intra-vial thermometry would provide monitoring of the status of the phase change in a sample, however the introduction of a thermometric probe directly into a sample would impose a very high risk of contamination. Therefore, in some embodiments of the instant invention, thermometric monitoring of the external surface temperature of the sample vial is applied to detect the initiation and the progression phase change, thereby circumventing the contamination risk imposed by intra-vial thermometric sensing. Although the thermometric data collected by external vial temperature measurements is subject to variance near the completion of the phase change due to stochastic movements of the solid sample remnant, locating the thermometric sensor to the lower portion of the vial or to the under surface of the vial would avoid the temperature fluctuations imposed by random motion of the solid phase remnant as the solid phase, being less dense than the liquid phase, will float within the vial thereby being excluded from the lower regions of the sample vial. Therefore in some embodiments, the instant invention comprises an external vial surface thermometric sensor that is located at the mid to upper exterior surface of the sample vial while in other embodiments the thermometric sensor is located at the mid to lower surface, including the undersurface of the sample vial exterior. In some embodiments, external vial surface thermometry is use to determine the start of the sample phase change while in other embodiments, external vial surface thermometry is use to determine both the start and termination of the phase change.

Figure 14:
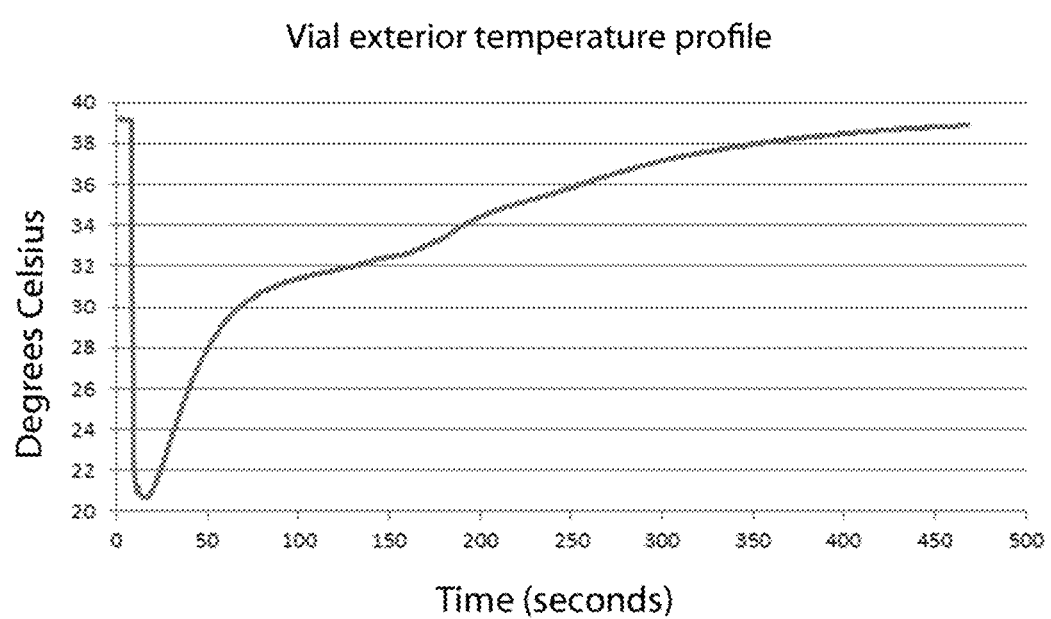
FIG. 14 shows temperature profile collected by a thermocouple that is placed in contact with the exterior wall of a thawing sample vial as described in FIG. 1. The warming block used was a split-block model and the initial vial temperature was −77° C.

Now referring to FIG. 14, a time-temperature trace collected from a thermocouple in contact with the sample vial exterior at a level opposite to the approximate mid-sample level of the internal 1 ml sample during the thawing cycle process, as described in FIG. 13, is shown. In the external temperature trace, as the thermally isolated thermocouple (part 130 in FIG. 1) contacts the −77° C. vial exterior, the temperature of the sensor declines rapidly until the sensor thermally equilibrates with the vial exterior at the temperature minimum occurring at the 11 second time point. As the temperature of the vial increases, the external temperature trace shows a deviation at approximately 60 seconds where the phase change is known to begin. The trace rises in a shallow slope until approximately 160 seconds where the completion of the phase change is known to be coincident.

The time-temperature traces collected using an intra-vial temperature sensor or an exterior surface temperature detector may be divided into three regions. The first region coincides with the time interval in which the contents of the vial are in the solid phase, the second coincides with the time interval where the vial contents are mixed solid and liquid phase and the third time interval coincides with the region where the vial contents are liquid phase exclusively. During the first and third regions, where the vial contents are one of two homogenous phases, the combined mass of the vial and the vial contents behave as a lumped capacity system, and the temperature transition behavior may be described by a linear time invariant equation:

$$T(t) = T_h + (T_c - T_h)e^{\frac{-(t-t_{pc})}{\tau_v}}, \quad \text{Equation 1}$$

wherein T(t), the temperature of the system at time t, may be determined by the above function wherein $T_h$ is the bath temperature, $T_c$ is the starting temperature of the vial, $t_{pc}$ is the time offset (required to mathematically match the calculated values to the actual data plot), and $\tau_v$ is the effective thermal time constant of the vile and contents. The formula describes the warming of a mass subject to a fixed temperature at its outer boundary. An example of fitting this equation output to the external vial temperature data presented in FIG. 14 is shown in FIG. 15.

The warming of the solid phase content of the vial between the point where the sensor reading reaches a minimum at approximately 11 seconds after the insertion of the vial into the warming block until a time of approximately 60 seconds can be closely approximated using the Equation 1 above where the value of 11 is the warm block temperature (39° C.), $T_c$ is the temperature selected at the beginning of the solid phase warming curve at a time after the vial surface sensor and the vial have reached thermal equilibrium, and at the time point where the value of the effective thermal time constant reaches a minimum value (23.8° C.), at 31 seconds past the time of insertion of the vial into the warm block. The value of the time constant $\tau_v$ may be calculated from the value of $T_h$ and the values of T(t) by the following derivation:

$$T(T) - T_h = (T_c - T_h)e^{\frac{-(t-t_{pc})}{\tau_v}} \quad \text{Equation 2)}$$

$$\frac{dT(t)}{dT} = -\frac{(T_c - T_h)}{\tau_v}e^{\frac{-(t-t_{pc})}{\tau_v}} \quad \text{Equation 3)}$$

Therefore, $$\frac{T(t) - T_h}{\frac{dT(t)}{dt}} = -\tau_v \quad \text{Equation 4)}$$

By applying a least regression slope analysis of the temperature data over the time data from a cluster of approximately 5 or 6 time points from the time-temperature data received from a temperature sensor in contact with the exterior of the vial, the denominator of equation 4 may be obtained. Likewise, by averaging the vial exterior temperature values from the same data cluster and subtracting the $T_h$ value, the numerator of equation 4 may be obtained. The $\tau_v$ value may then be obtained by taking the negative value of the division result. The $\tau_v$ value obtained by this treatment of the data will only relate to the linear time-invariant equation that describes the lumped capacity system of the vial and the solid sample during the portion of the curve prior to the commencement of the phase change, and therefore a deviation from a constant $\tau_v$ value in excess of a pre-set limit may be used to identify the beginning of the phase change.

Figure 15A:
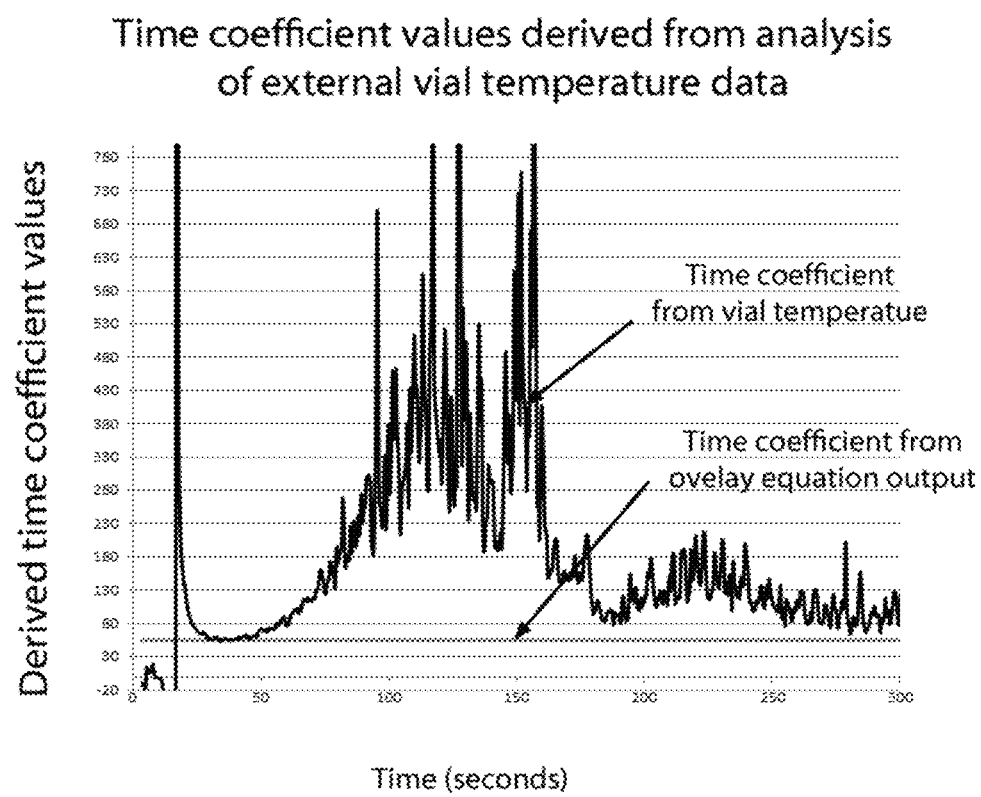
FIG. 15A, part A shows a graph of the time constant value output from an equation using the external vial temperature data shown in FIG. 14 as input. Also shown is a graph of the same equation using as input values a linear time invariant (LTI) equation with variables adjusted to match the solid phase portion of the data in the graph shown in FIG. 14.

Now referring to FIG. 15A, a time graph of the $\tau_v$ values for the example data set shown in FIG. 14 is presented (dark trace). In the value plot it can be seen that in the range of 31 to 50 seconds into the warming process, the $\tau_v$ values hold a minimum value of approximately 55 seconds. In addition, the time graph is shown (light grey line) of the $\tau_v$ values obtained by an identical treatment of the output of the linear time invariant (LTI) equation in which the input values of the constants were $T_h$=30° C., $T_c$=23.8° C., $\tau_v$=55 seconds (as determined for the experimental data in FIG. 15), and the $t_{pc}$ time offset value is 32 seconds, as determined by a regression analysis fit of the LTI equation to the data set of FIG. 14 in the region of 31 to 50 seconds. As may be expected, the $\tau_v$ value for the LTI equation does not change over time. Comparing the two sets of $\tau_v$ values in FIG. 15A, it may be seen that a prediction of the beginning of the phase change in the contents of the test vial at approximately 50 seconds may be determined by the deviation of the $\tau_v$ values for the experimental data from the theoretical $\tau_v$ value. Therefore in some embodiments, a data processing algorithm is embedded into the software of the instant invention to determine the beginning of the phase change of the contents of a vial. By adding a time offset value to the beginning of the phase change time value based upon the following equation, the time of the phase change completion may be estimated. Using equation 5 below, the duration of the thaw ($T_{thaw}$) may be calculated where $\Delta H_f$ is the specific heat of fusion of the sample, $m_{soln}$ is the mass of the sample, $R_v$ is the absolute thermal resistance of the sample vial wall, $T_{vial}$ is the temperature of the vial exterior wall, and $T_m$ is the melting temperature of the sample.

$$T_{thaw} = \frac{\Delta H_f \cdot m_{soln} \cdot R_v}{T_{vial} - T_m} \quad \text{Equation 5)}$$

As a typical biological sample stored in a cryogenic sample vial is an aqueous solution, the melting temperature is not a single value as would be the case for a homogenous material, but rather a temperature range. Nevertheless, refinement of equation 5 by experimental determination of a value of $T_m$, for a specific vial, that will allow a fit with the actual $T_{thaw}$ value will provide a more accurate means of predicting the $T_{thaw}$ value for different sample masses. However, as was shown in FIGS. 12 and 13, the rate of thermal energy influx in a thawing sample contained within a sample vial is largely independent of the sample volume and therefore of the sample mass. Therefore, in some embodiments of the instant invention the termination of the phase change is determined by a software algorithm that combines the time value calculated for the start of the phase change as described above with an experimentally derived phase change duration value for a given sample vial to determine the phase change completion time. In other embodiments the reduction of the determined phase change completion time value by a constant will be used to terminate the thawing process while some solid phase is still remaining in the vial.

Figure 15B:
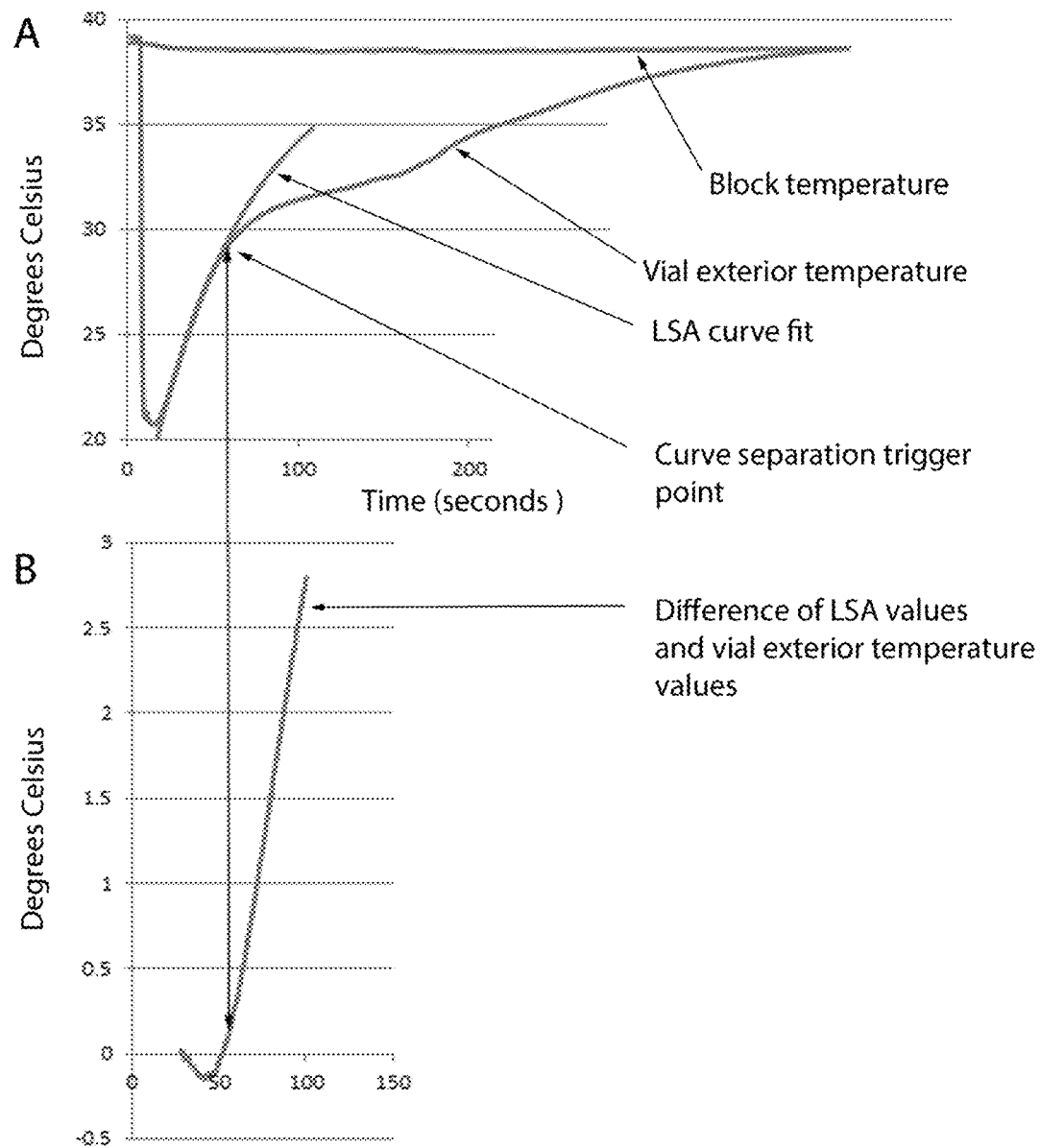
FIG. 15B shows a graphic, Part A, of a linear time invariant (LTI) lumped system analysis (LSA) curve with variable parameters adjusted to overlay the solid-phase portion of a temperature-time plot using data collected from a thermocouple that is placed in contact with the exterior wall of a thawing sample vial as described in FIG. 1. Part B of FIG. 15 shows a temperature time graph of the difference between the output of the fitted LSA equation output in part A and the actual temperature data collected for that time point. The graph indicates the time point where melting of the sample begins, as determined by the plot in graph B exceeding a selected pre-set value limit of 0.2.

Now referring to FIG. 15B, an alternative data treatment by which the beginning of the phase change may be determined is shown. In FIG. 15A, part A, the plot of the experimental vial exterior temperature described in FIG. 14 is indicated along with the warming block temperature trace for the same experiment. A plot of a LTI equation output values that overlays the solid phase portion of the warming sequence is shown imposed on the experimental data. The variable values for the LTI equation as described in equation 1 above were derived from the warming block temperature ($T_h = 39°$ C.), the minimum $\tau_v$ value following the vial surface temperature sensor equilibrium, as determined by equations 2-4 above, and the temperature of the vial surface at the time where the minimum $\tau_v$ value was first observed ($T_c = 23.8°$ C.). The $t_{pc}$ value was determined by iterative refinement such that a minimum value was identified for the difference between the LTI equation output and a linear regression analysis of vial surface temperature data points following the time of detection of the minimum $\tau_v$ value.

Now referring to FIG. 15B, part B, a graph of the difference between the experimental data and the output of the LTI equation is shown with respect to time. The vertical arrow located at approximately 60 seconds indicates the point where the experimental data and the calculated LTI equation data diverge by a selected value of 0.2° C. In some embodiments of the instant invention, the embodiment of the above divergence gate in the algorithmic software will determine the beginning of the phase change.

Figure 16:
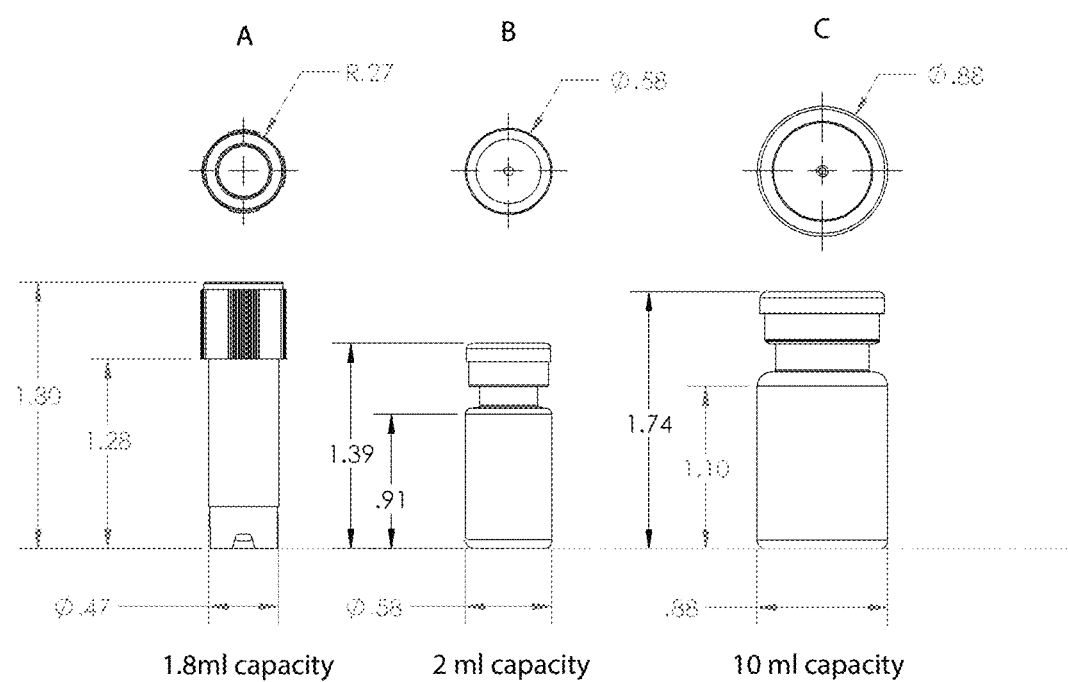
FIG. 16 shows the dimensions of three representative sample vials that may, without limitation, be thawed using the instant invention. The vials include (A) a screw-cap cryo-storage vial with a nominal capacity of 1.8 ml, (B) a septum-cap vial with a nominal capacity of 2 ml, and (C) a septum-cap vial with a nominal capacity of 10 ml.

Now referring to FIG. 16, without limitation, the dimensions of three sample vial types that may be used the instant invention are shown. In some embodiments of the invention, the warming blocks (2008 and 2010 in subsequent FIG. 20) may be adjusted in the dimensions of the vial receiver well (2033 in subsequent FIG. 20) to accommodate the difference in the sample vial dimensions shown, thereby allowing the adaptation of a common design of the instant invention to be applied to multiple sample vial types. The sample container may be any cryogenic vial. For example, the sample container may be a standard 5.0 mL vial, 4.0 mL vial, 2.0 mL vial, 1.2 mL vial, 500 µL vial, etc. The vials may be constructed out of polypropylene or other materials, for example, and may be round bottomed or self-standing. The sample holder may be in heat-transferring contact with the side-walls of a received vial. Optionally, the sample holder may be configured to limit the heat transfer from the top or bottom of a sample container. While the sample container is generally described as a vial, it should be understood that samples in other containers may be thawed using methods and systems described herein. For example, the container may be a bag or other vessel as desired.

In other embodiments, the warming blocks may comprise a single vial receiver well dimension that may be fit to accommodate multiple vial types and dimensions by comprising an adaptor part.

Figure 17:
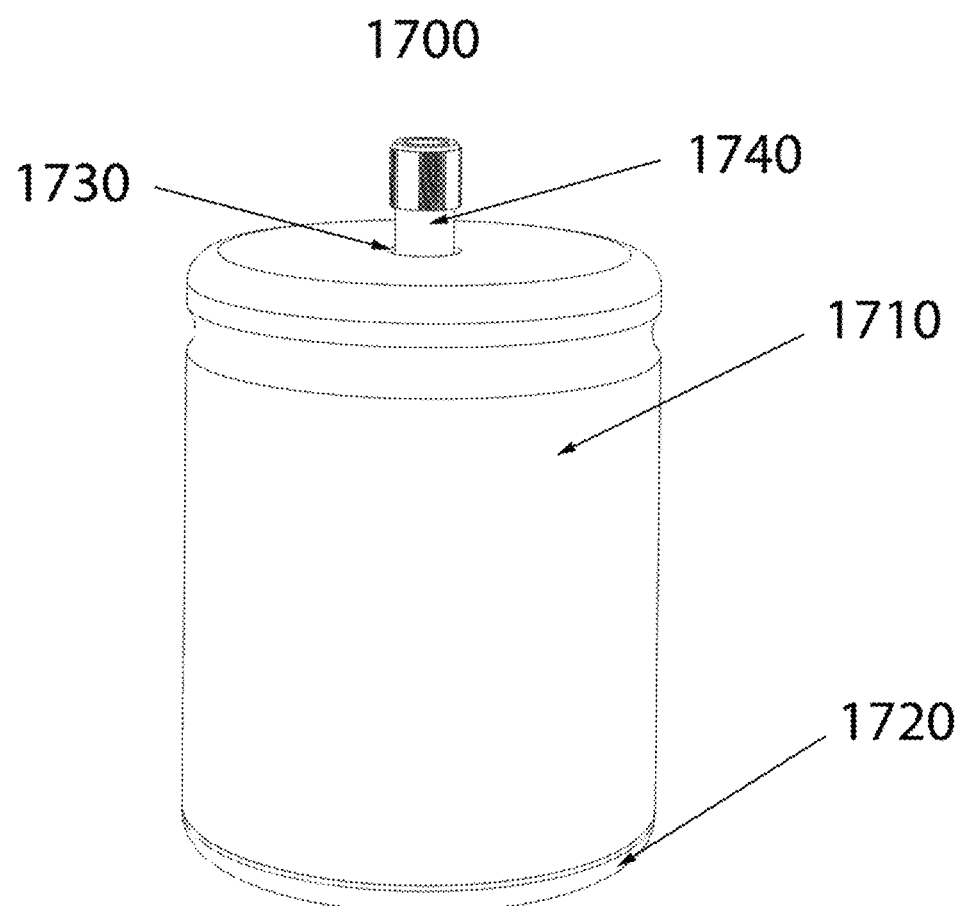
FIG. 17 shows the exterior of a representative embodiment of the invention.

Now referring to FIG. 17, the exterior of a representative embodiment of the invention is shown. The embodiment is presented as a functional example of the invention only and is not intended to limit alternative embodiments of the invention. The figure identifies the cover 1700 for the internal mechanism that comprises an external upper shell 1710 and a clear or translucent base 1720. In this embodiment, the uses inserts a sample vial 1740 into the available top opening 1730 to begin the warming sequence. When the vial insertion achieves a specific depth, the internal mechanism triggers the rapid closure of an open segmented warm block that will contact and hold secure the sample vial during the warming process.

Figure 18:
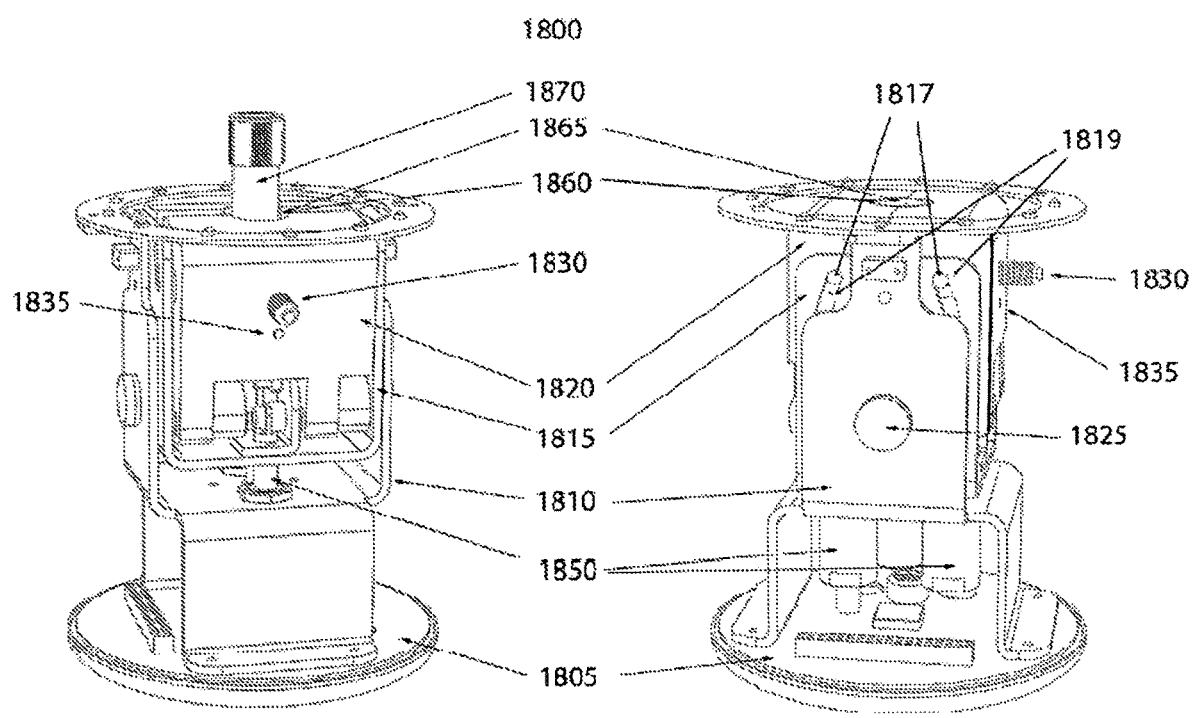
FIG. 18 shows two perspectives of a representative embodiment of the interior mechanism of the device shown in FIG. 17.

Now referring to FIG. 18, two views of an embodiment of the internal mechanism 1800 are shown. In this embodiment, the main frame 1810 is connected to a two part warming block 1820, the two parts of which are identical and joined by a 180-degree rotation of one part relative to its mating part. The two block halves are joined by a hinge pin 1825 such that the two warming block parts may rotate and separate to a 10-degree included angle between the vertical plane median faces of the parts. The two block halves are articulated about the hinge axis 1825 by a sliding spreader frame 1815 which engages pin shafts 1817, embedded in the warming block parts 1820 on both sides of each part, through angles slots 1819 such that when the sliding spreader frame 1815 ascends and descends relative to the main frame 1810, the slots 1819 open and close the warming block halves 1820. The sliding spreader frame 1815 is articulated by two solenoid actuators 1850, one configured to elevate the spreader frame 1815 when activated and one configured to de-elevate the spreader frame relative to the main frame 1810. The two warming block halves 1820 comprise a central vial receiving well 1865 which is divided in a vertical plane that is coincident with the vertical plane separating the two warming block halves. The central vial well extends through the entirety of the warming blocks and comprises a 2 mm-thick lining of thermally conductive foam 1860 that covers the entire inner surface of the central vial well to a depth of 1.1 inches below the top surface of the warming block. A thermistor temperature sensor 1835 is embedded in both of the warming block parts and the temperature data signals are conducted to the microprocessor board 1805 via wire connections (not shown). One or both of the warming blocks comprise an additional temperature sensor 1830 that is thermally isolated from the warming block 1820 and rests in contact with the exterior surface of the sample vial 1870 when the sample vial is inserted into the central vial well and the warming block jaws 1820 are closed. The data signal from the sensor 1830 is conducted to the microprocessor board 1805 by connector wires (not shown).

Figure 19:
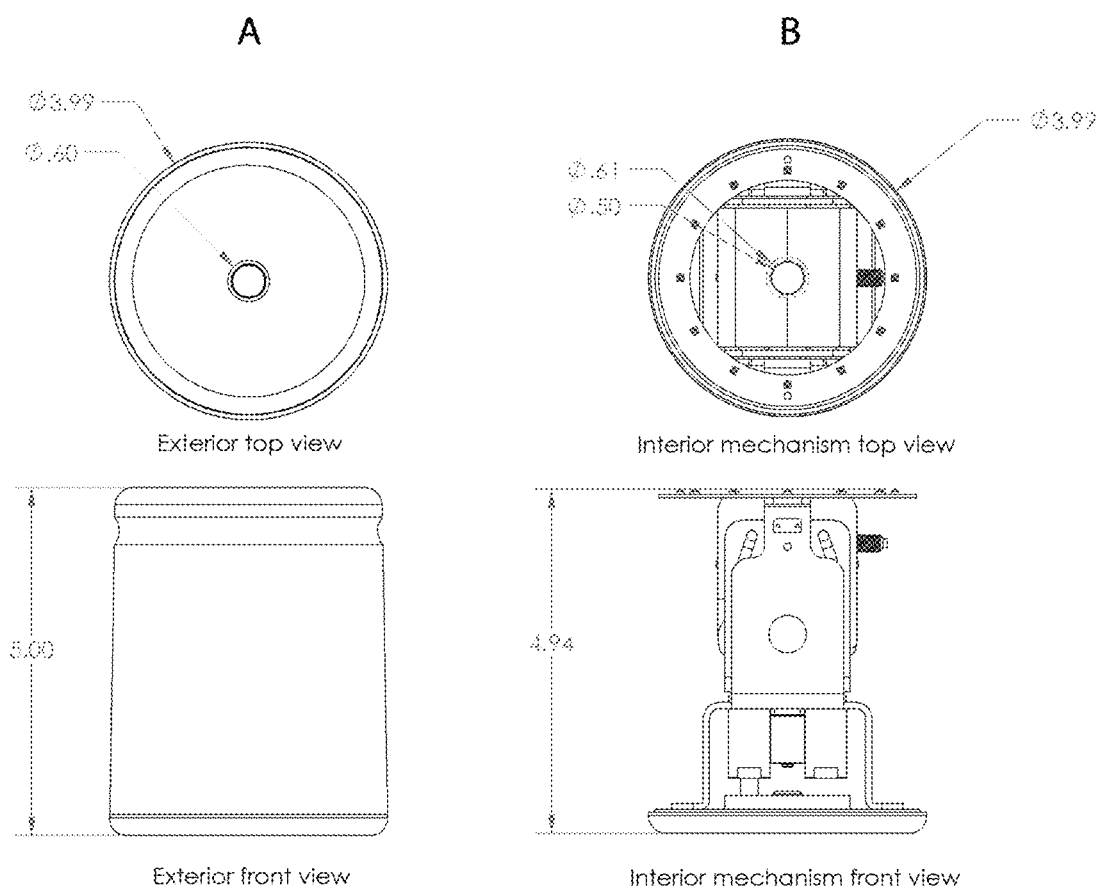
FIG. 19 shows the overall dimensions of the embodiments of the invention shown in FIGS. 17 and 18.

Now referring to FIG. 19, the overall dimensions of the embodiment shown in FIG. 18 are shown. The exterior shell shown in part A has a height of 5 inches and a major diameter of approximately 4 inches. The top opening access for the vial receiver well has a diameter of approximately 0.6 inches. The in inner mechanism shown in part B has an overall height of approximately 4.9 inches, a major diameter of approximately 4 inches, and a vial receiving well diameter of approximately 0.5 inches.

Figure 20:
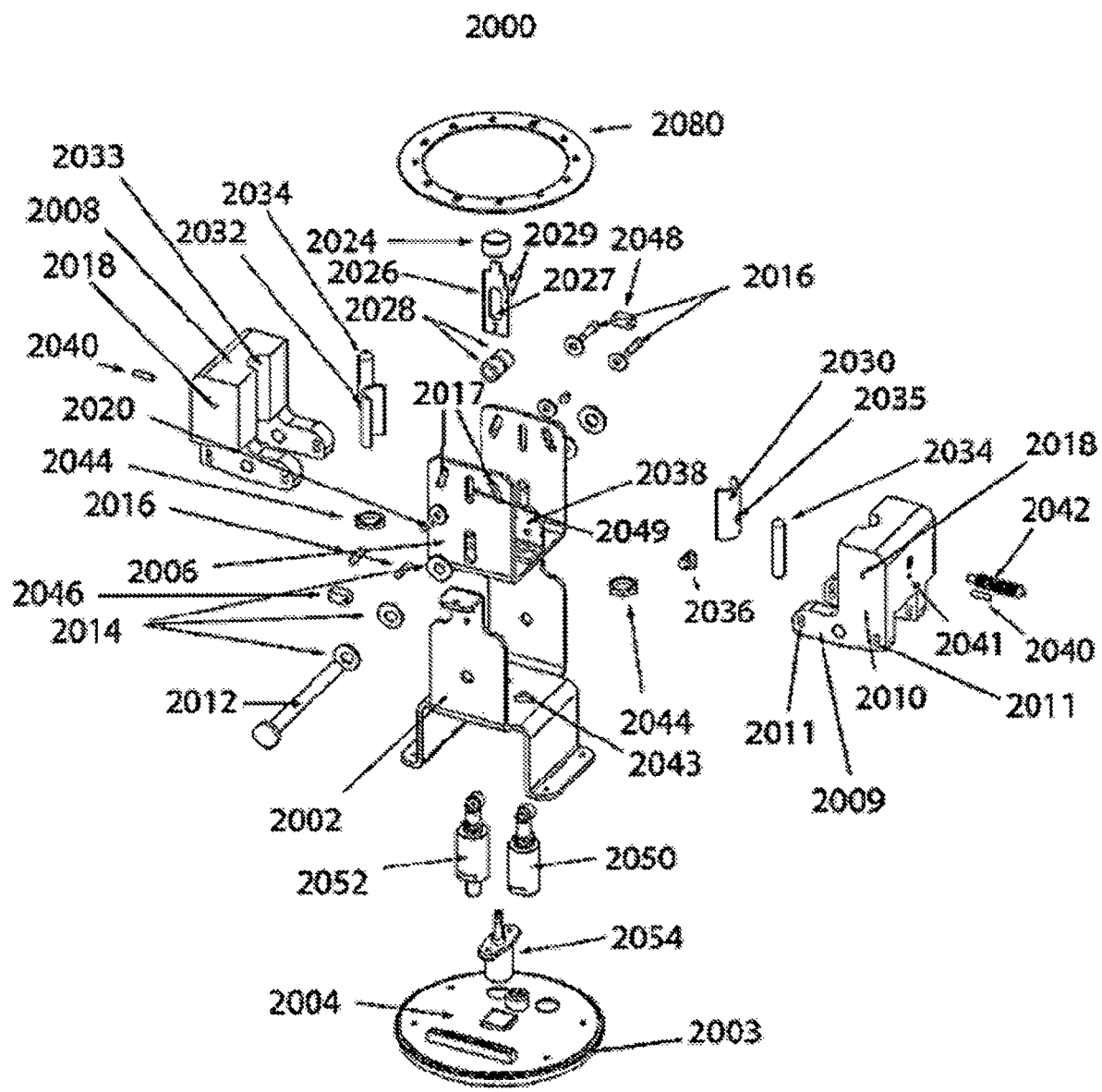
FIG. 20 shows an exploded view of the embodiment shown in FIG. 18.

Now referring to FIG. 20, an exploded view 2000 of the embodiment shown in FIGS. 18 and 19 is shown. In this diagram, the main frame 2002 supports the remaining parts of the internal mechanism and is joined to the base part 2003 by fasteners (not shown) that extend through the microprocessor circuit board 2004. The two warming block halves 2008 and 2010 are joined to the main frame 2002 by the hinge pin 2012. The warming block halves rotate on the hinge pin 2012 and are thereby restricted to a range of motion from a closed position in which the median plane faces are parallel to an open position where the median plane faces are separated with an included angle of 10 degrees. The arm extensions 2009 of the warming block halves comprise cylindrical holes 2011 that may optionally receive cylindrical magnets (not shown) that when installed will mate with magnets installed on the opposite warming block part in a manner that will provide a holding force hold the warming block jaws in either an open or closed position in the absence of articulation or holding forces applied by other components in the embodiment. The two warming block jaws 2008 and 2010 are articulated by a sliding spreader frame 2006 that engages the warming blocks through angled slot features 2017 that engage pin bearings 2016 that are embedded in the warming block recesses 2018. The slots 2017 in the sliding spreader frame are angled such that when the sliding spreader frame is raised relative to the main frame the warming blocks rotate on the hinge pin 2012 and open to an angle of 10 degrees. When the sliding spreader frame is lowered relative to the main frame, the warming blocks rotate to a closed orientation where the inner vertical face are parallel. The position of the sliding spreader frame in relation to the main frame is monitored by an optical sensor 2048 that detects a light signal from a light source 2046, both of which are mounted to the main frame. When the sliding spreader frame is raised, the light signal from the source 2046 has an unobstructed path through the slot 2049 in the sliding spreader frame and through the open warming block parts provided there is no other obstruction in the central vial receiver such as a sample vial. When the sliding spreader frame is lowered in relation to the main frame, the light from source 2046 is blocked by the sliding spreader frame. The light source 2046 and the light detector 2048 receive power from the microprocessor circuit board 2004 through power wires (not shown) and the microprocessor receives a digital signal from the optical sensor 2048 through wire conduits (not shown). The sliding spreader frame 2006 is articulated by solenoid activators, one that elevates the spreader frame when activated 2052, and one that de-elevates the spreader frame when activated 2050. The solenoid actuators are joined to the sliding spreader frame through an L-bracket 2038 that is fastened to the spreader frame and to the main frame through holes 2043 and fastened by a hex nut 2044. Two thermally conductive foam pads 2030 and 2032 line the two halves of the central vial receiving well 2033 in the warming blocks 2008 and 2010. One or more of the foam pads 2030 and 2032 comprise a passage 2035 through which a temperature sensor 2042 embedded in the warming block(s) may pass through to contact the exterior surface of a sample vial contained between the foam pads 2030 and 3032 within the vial receiving well of the blocks. Each of the warming blocks 2008 and 2010 comprise one or more heater elements 2034 that is received into a cavity in the underside of the warming block parts (not visible). The temperature of the warming blocks 2008 and 2010 is sensed by one or more temperature sensors 2040 that are embedded in the warming block in a receiver cavity 2041 and secured by a perpendicular set screw (not shown). A central pedestal 2024 is positioned in a coaxial orientation to the central vial receiving well and is mounted on a sliding support 2026 that comprises a slot through which the hinge pin 2012 passes thereby capturing and laterally constraining the sliding support. The sliding support is further restrained and supported by two bushing bearings 2028 through which the hinge pin passes and that are positioned on either side of the sliding support flat surfaces. The sliding support is further constrained to a vertical linear motion by joining with the sliding shaft of a motion damper 2054 that is mounted to the underside of the main frame 2002. The sliding support 2026 further comprises a notch 2029 and hole 2027 which, depending on the elevation of the part, allows or blocks an light signal of an optical sensor 2036 that is mounted on the L-bracket 2038. Depending upon the relative positions of the sliding pedestal support 2026 and the sliding spreader frame 2006, a high and low digital signal from the optical sensor 2036 may indicate one of four positions states when combined with the vertical position signal from the sliding spreader frame position sensor 2048: 1) sliding support 2026 raised; sliding spreader frame 2006 raised, 2) sliding support 2026 lowered; sliding spreader frame 2006 raised, 3) sliding support 2026 lowered; sliding spreader frame 2006 lowered, and 4) sliding support 2026 raised; sliding spreader frame 2006 lowered (a fault condition as described in subsequent figures). The damper 2054 in some embodiments comprises a spring (not shown) that is configured such that when the pedestal 2024, the sliding support 2026, and the damper shaft are lowered, the spring is compressed and provides a force that can restore the parts to the lifted position. In some embodiments the lifting motion resulting from the spring force opposed only by the friction force of the conductive foam 2030 and 2032 contact with the sample vial exterior, while in other embodiments, the lifting spring force is controlled by actively regulated mechanical restrictors, such as, but not limited to, solenoid latches. In alternative embodiments, the lifting force is provided partially or exclusively by actively controlled actuators such but not limited to solenoids and motors. Some embodiments comprise a user interface including, but not limited to, LED lights and light arrays, LCD screens, keypads, button switches, sliding switches, touch screens, knobs, slide switches, capacitive switches, and wireless linkage to remote control interfaces. In the embodiment shown in FIG. 20, a radial array of LED lights 2080 is fixed to the main frame that will be visible through the outer shell (not shown) through translucent shell material. The LED array illumination may be controlled by the microprocessor board 2004 through a ribbon wire connector (not shown) and may indicate the thawing status of the sample vial, states of readiness, and error codes. While illustrated with the lights positioned on a top surface of the device, it should be understood that other embodiments may include an LED array on a side of the device. In some embodiments, the microprocessor board comprises data ports by which the microprocessor may transmit stored data or may receive a data stream from an external source, for example for the purpose of installing software updates.

Figure 21:
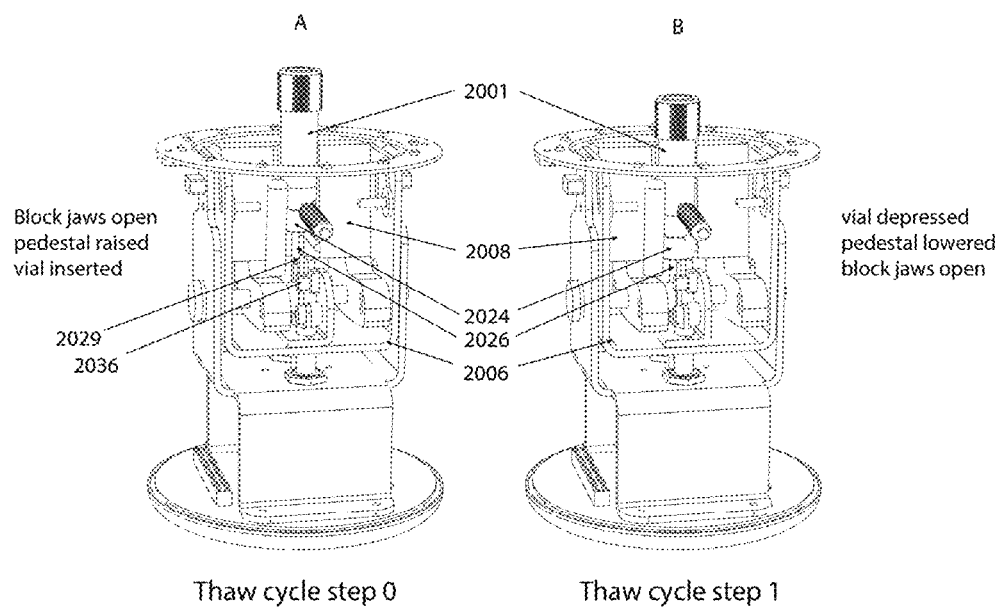
FIG. 21 shows the first two steps (step 0 and step 1) of the thawing cycle of the embodiment shown in FIGS. 17 through 20. In the two-step illustrations (and in FIGS. 22 and 23), the front-most heater block half is shown removed to better reveal the mechanism positions and action during the six cycle steps.
Figure 22:
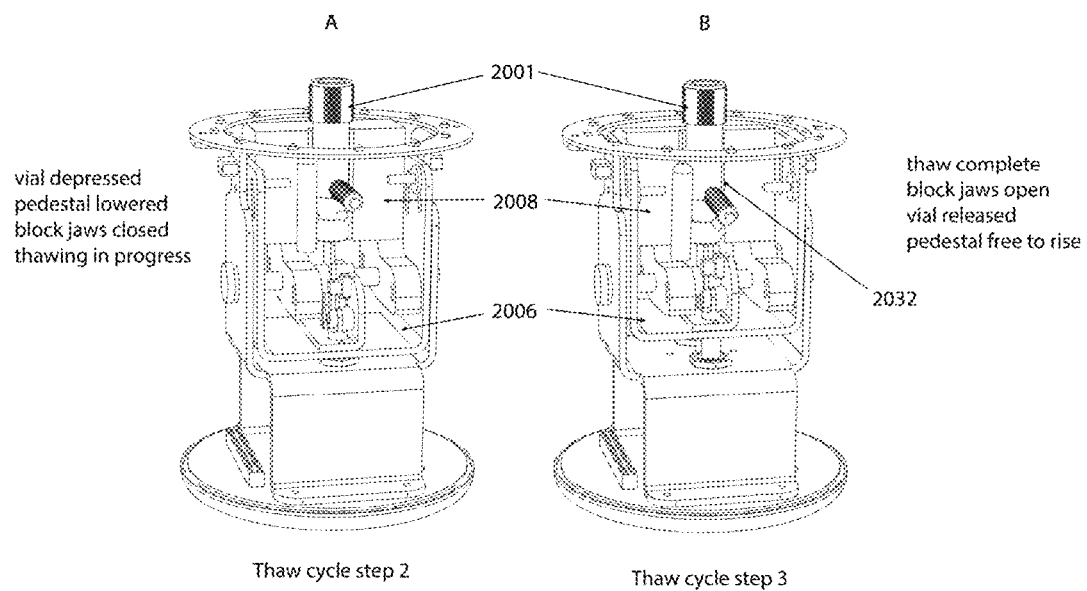
FIG. 22 shows the subsequent two steps, step 2 and step 3, of the thaw cycle to those illustrated in FIG. 21.
Figure 23:
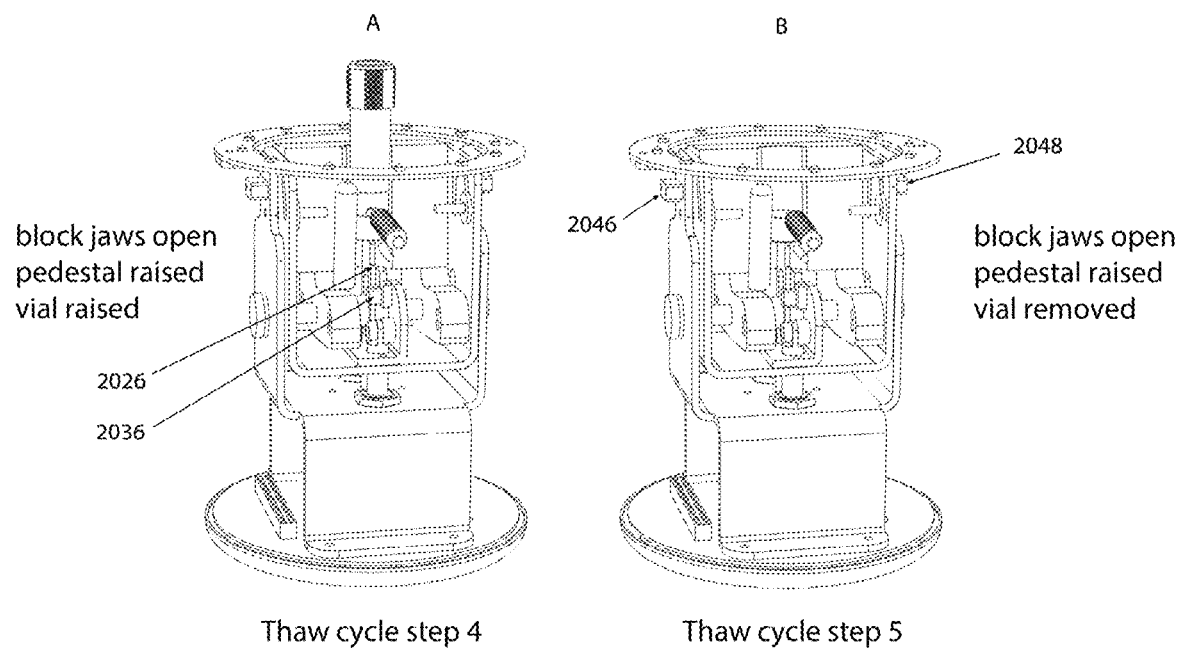
FIG. 23 shows the subsequent two steps, step 4 and step 5, of the thaw cycle to those illustrated in FIG. 22.

Now referring to FIGS. 21-23, an example of the operation sequence of the embodiment shown in FIGS. 19 and 20 is shown. In FIGS. 21-23, the embodiment is displayed with the forward warming block removed so that the internal mechanism and position of the parts may be illustrated. Following previous temperature equilibration to −77° C. by placing the sample vial 2001 in a temperature equilibration apparatus such as those described in the embodiments shown in FIGS. 2-5 for a period of ten or more minutes, the thawing cycle is initiated by insertion of a sample vial 2001 into the warming block vial receiving cavity as shown in FIG. 21, part A. In this state, the warming block has been previously temperature-equilibrated to the appropriate warming temperature, the sliding support frame 2006 is raised and the warming blocks 2008 and 2010 (not shown) are open. In thaw cycle step 1, shown in FIG. 21, part B, the sample vial is manually depressed, lowering the pedestal 2024 and sliding support 2026 until the sliding support optical trigger 2029 passes the optical sensor 2036. Now referring to FIG. 22, part A. Sensing that the sample vial has descended to the appropriate depth, the microprocessor board activates the solenoid (2050 in FIG. 20) to lower the sliding spreader frame 2006, thereby closing the warming blocks on the sample vial 2001, initiating the process of thermal energy transfer to the vial and contents.

Now referring to FIG. 22, part B, the thawing process having been completed, the microprocessor activates the lifting solenoid (2052 in FIG. 20) to raise the sliding spreader frame 2006, thereby opening the warming blocks 2008 and 2010 (not shown) releasing the restraining friction between the conductive foam liner, 2030 (not shown) and 2032, and the vial. The opening of the warming blocks disrupts the thermal conduction pathway from the conductive foam thereby preventing or significantly delaying an undesired temperature rise in the vial contents.

Now referring to FIG. 23, part A, the friction restraint upon the vial now disrupted, the sliding support 2026 and the vial support pedestal 2024 now raise and present the sample to the operator and as the sliding support optical trigger 2029 passes the optical sensor 2036, the microprocessor receives a signal that the vial has been presented. Now referring to FIG. 23, part B, when the vial is removed from the warming block vial receiver, the light pathway between the optical light source 2046 and the optical sensor 2048 becomes unobstructed and the microprocessor receives a signal that indicates that the vial has been removed, thereby preventing algorithmic activation of alert and alarm signals.

Figure 24:
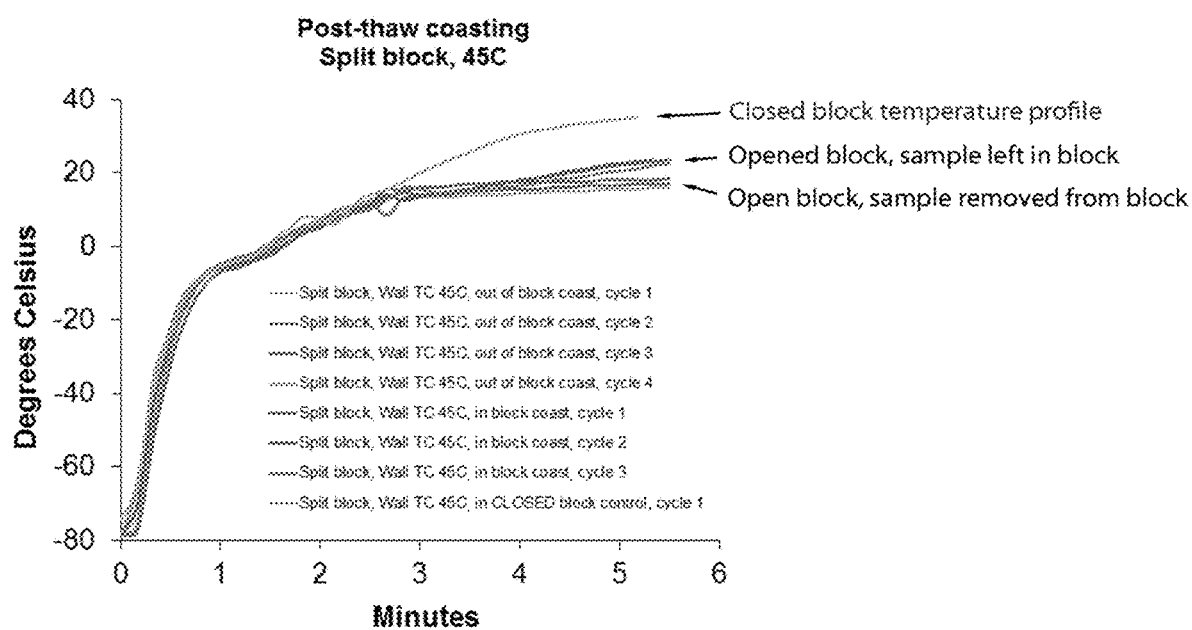
FIG. 24 shows a time-temperature plot of two series of thawing profiles, the first series in which the jaws of the 45° C. warming block were opened 150 seconds into the thaw and the vial was left in-situ in the warming block, and a second series in which the jaws of the warming block were opened 150 seconds into the thaw and the vial was removed from the warming block and held at room temperature. A comparative trace from a vial that was left in the 45° C. block with the jaws closed for approximately 5 minutes is also shown.

Now referring to FIG. 24, a graphic plot time-temperature plot of a thawing experiment series is shown to demonstrate the effectiveness of opening the warming blocks upon the termination of the thawing process in interrupting the thermal energy flow into the sample. In this experimental series, repeated cycles of vial freezing in liquid nitrogen, equilibration in the apparatus described in FIGS. 2 and 3, and insertion into a 45 degree warming block of the design described in FIGS. 7 and 8, and the internal temperature of a 1 ml sample payload monitored by the insertion of a thermocouple sensor held in a position near to the internal wall of the vial to a position at half the height of the sample. In one test cycle, upon termination of the thaw as determined by time measurement, the warming blocks were left closed and the vial allowed to remain in the warming block for a total interval of approximately 6 minutes. In this experiment, the temperature of the sample continues to rise toward the block temperature. In a second cycle series, the sample vials upon completion of the thaw, the warming block was opened and the vials were removed from the warming block and held in open air for a total duration of approximately 6 minutes. In this data set, the temperature of the sample increased very little over the three-minute interval following the block opening. In a third cycle series, the previous experiment was repeated with the exception that the vial was allowed to remain in the warming block following the opening of the warming block. In this series, the temperature of the vial contents increased at a slightly higher rate that when the vial was removed from the block upon the termination of the thaw, however the increase in temperature was significantly less than that observed when the warming block was left closed upon termination of the thaw. The experiment set strongly supports the benefit of interrupting the thermal conduction pathway between the warming block and the sample vial to terminate the thermal energy influx into the sample upon the completion of the thaw process. In some embodiments of the instant invention, the warming process following insertion of a sample vial into the warming block receiving well is terminated by the introduction of air space between the solid material of the warming block and the exterior surface of the sample vial. In some embodiments, the system may be configured to maintain the sample at a desired temperature at the end of the thawing.

In some embodiments, multiple algorithms may be provided for determining a thaw end time. Optionally, each of the multiple algorithms may be concurrently run to provide separate estimates for the thaw end time. The system may be configured to end the thawing based on the algorithm which first provides an estimated thaw end time. Optionally, the system may be configured to allow each of the algorithms to complete their estimations and may utilize the shortest thawing interval calculated. In further embodiments, a system may be configured to average the estimated thawing intervals and utilize the averaged thawing interval to determine the thaw end time.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A device for the conversion from a solid state to liquid state of a sample contained in a vessel, the device comprising:
   a pliable solid material forming a receptacle for receiving the vessel;
   a non-pliable solid material configured to form a cavity, wherein the pliable solid material forms a lining within the cavity, and wherein, with the vessel received within the receptacle formed by the pliable solid material, the pliable solid material is interposed between the vessel and the non-pliable solid material;
   a heater configured to heat the pliable solid material through the non-pliable solid material to a temperature higher than a melting point of the sample;
   a temperature sensor fixed in, and thermally insulated from, the non-pliable solid material, wherein a temperature signal reported by the temperature sensor is proportional to a temperature of contents within the vessel;
   a processor configured to control the heater;
   a micro-controller configured to deliver a first control signal to interrupt heating at a calculated thaw end time, wherein:
      the sample at the calculated thaw end time has solid phase remaining in an aqueous solution in the vessel, and the calculated thaw end time is determined using a predictive thawing model following the equation $$T_{thaw} = \frac{\Delta H_f \cdot m_{soln} \cdot R_v}{T_{vial} - T_m}, \quad \text{Equation 5)}$$

wherein $T_{thaw}$ represents a calculated duration for thawing the sample, wherein $\Delta H_f$ represents the sample specific heat of fusion, wherein $m_{soln}$ represents the sample mass, wherein $R_v$ represents absolute thermal resistance of a vessel wall, wherein $T_{vial}$ represents temperature of a vessel exterior wall reported by the temperature sensor, and wherein $T_m$ is the sample melting temperature.

2. The device of claim 1, wherein the pliable solid material has a thermal conductivity greater than 0.5 Watts per meter-Kelvin and the non-pliable solid material has a thermal conductivity between 10 Watts per meter-Kelvin and 410 Watts per meter-Kelvin.

3. The device of claim 1, wherein the pliable and the non-pliable solid material form two or more separate segments that join together to form the receptacle and the segments are joined by a mechanical linkage configured to move the segments into an open configuration for receiving or releasing the vessel and a closed configuration for forming the receptacle and heating the vessel, and wherein the pliable solid material is arranged to be selectively placed in contact with the vessel when transitioning the segments from the open configuration to the closed configuration or removed from contact with the vessel when transitioning the segments from the closed configuration to the open configuration.

4. The device of claim 3, further comprising a clamp for imposing a clamping force on the segments on the vessel contained within the receptacle, where the clamping force is imposed by magnetic, electromagnetic, hydraulic, pneumatic, or mechanical forces, or any combination thereof.

5. The device of claim 3, further comprising a vessel sensor for detecting the presence of the vessel between the segments of the pliable solid material with the segments in either the open configuration or the closed configuration.

6. The device of claim 3, wherein, with the segments in the open configuration, the micro-controller is configured to detect a placement of the vessel at a position between the segments while the segments are in the open configuration and configured to deliver a second control signal to actuate the mechanical linkage to move the segments toward the closed configuration to contact the vessel with the pliable solid material of the segments upon insertion of the vessel into the position between the open segments.

7. The device of claim 3, wherein, with the segments in the closed configuration and heating the vessel, the micro-controller is configured to interrupt heating of the vessel by delivering the first control signal to actuate the mechanical linkage to move the segments toward the open configuration such that the pliable solid material of the segments do not contact the vessel.

8. The device of claim 3, wherein the pliable solid material is arranged to eliminate air gaps between the vessel and the segments in the closed configuration.

9. The device of claim 1, wherein the calculated thaw end time is determined by algorithmic analysis of the temperature signal from the temperature sensor reporting an exterior surface temperature of the vessel, wherein the temperature sensor is located at a position at a lower region of the exterior surface of the vessel below the top level of the sample contained therein.

10. The device of claim 1, wherein the calculated thaw end time is determined using a calculated time value for the start of a phase change from solid to liquid.

11. The device of claim 10, wherein the calculated time value is determined by identifying a deviation of temperature signals from temperatures predicted by a linear equation specific to the sample.

12. A device for the conversion from a solid state to liquid state of a sample contained in a vessel, the device comprising:
a pliable solid material;
a non-pliable solid material configured to form a cavity, wherein the pliable solid material forms a lining within the cavity, wherein the pliable and the non-pliable solid material form two or more separate segments that join together to form a receptacle for receiving the vessel, and wherein, with the vessel received within the receptacle, the pliable solid material is interposed between the vessel and the non-pliable solid material;
a mechanical linkage, including a solenoid actuator, joining the two or more separate segments and configured to move the segments into an open configuration for receiving or releasing the vessel, and into a closed configuration for forming the receptacle and thawing the sample within the vessel;
a temperature sensor fixed in, and thermally insulated from, the non-pliable solid material;
a heater configured to heat the pliable solid material to a temperature higher than a melting point of the sample, and thereby heat the vessel received within the receptacle;
a processor configured to control the heater, and
a micro-controller configured to output a first control signal at a calculated thaw end time to the solenoid actuator to raise the vessel and move the segments into the open configuration, thereby releasing the vessel and disrupting heat transfer from the pliable solid material to the vessel, wherein:
the sample at the calculated thaw end time has solid phase remaining in an aqueous solution in the vessel, and
the calculated thaw end time is determined using:
a calculated time value for the start of a phase change from solid to liquid, and
an experimentally derived phase change duration value for the vessel.

13. The device of claim 12, wherein the pliable solid material has a thermal conductivity greater than 0.5 Watts per meter-Kelvin and the non-pliable solid material has a thermal conductivity between 10 Watts per meter-Kelvin and 410 Watts per meter-Kelvin.

14. The device of claim 12, further comprising a clamp for imposing a clamping force on the segments on the vessel contained within the receptacle, where the clamping force is imposed by magnetic, electromagnetic, hydraulic, pneumatic, or mechanical forces, or any combination thereof.

15. The device of claim 12, further comprising a vessel sensor for detecting the presence of the vessel between the segments of the pliable solid material with the segments in either the open configuration or the closed configuration.

16. The device of claim 12, wherein, with the segments in the open configuration, the micro-controller is configured to detect a placement of the vessel at a position between the segments while the segments are in the open configuration and configured to deliver a second control signal to actuate the mechanical linkage to move the segments toward the closed configuration to contact the vessel with the pliable solid material of the segments upon insertion of the vessel into the position between the open segments.

17. The device of claim 12, wherein, with the segments in the closed configuration and heating the vessel, the microcontroller is configured to interrupt heating of the vessel by delivering the first control signal to actuate the mechanical linkage to move the segments toward the open configuration such that the pliable solid material of the segments do not contact the vessel.

18. The device of claim 12, wherein the temperature sensor is held in contact with the vessel at a contact location such that a temperature signal reported by the temperature sensor is proportional to a temperature of contents within the vessel.

19. The device of claim 12, wherein the temperature sensor is an infra-red temperature sensor, and wherein a temperature signal reported by the infra-red temperature sensor is proportional to a temperature of contents within the vessel.

20. The device of claim 19, wherein a total duration of a sample thawing interval is determined by algorithmic analysis of the temperature signal from the infra-red temperature sensor reporting an exterior surface temperature of the vessel, wherein the infra-red temperature sensor is located at a position at a lower region of the exterior surface of the vessel at a location below the top level of the sample contained therein.

21. The device of claim 12, wherein the heating of the pliable solid material causes radial heating of the vessel to achieve a thaw time that is predominantly independent of a vessel fill level.

22. The device of claim 12, wherein the pliable solid material is arranged to eliminate air gaps between the vessel and the segments in the closed configuration.

23. The device of claim 12, wherein the pliable solid material is arranged to be selectively placed in contact with the vessel when transitioning the segments from the open configuration to the closed configuration, or removed from contact with the vessel when transitioning the segments from the closed configuration to the open configuration.

24. The device of claim 12, wherein in the open configuration, the two or more separate segments form a "V" shape relative to each other.

25. The device of claim 12, wherein the calculated time value is determined using a linear equation.

* * * * *